(12) United States Patent
Deutsch et al.

(10) Patent No.: US 10,399,062 B2
(45) Date of Patent: Sep. 3, 2019

(54) HYDROGENATION AND ETHYNYLATION CATALYSTS

(71) Applicant: BASF Corporation, Florham Park, NJ (US)

(72) Inventors: Keenan Lee Deutsch, Highland Park, NJ (US); Rostam J. Madon, Flemington, NJ (US)

(73) Assignee: BASF Corporation, Florham Park, NJ (US)

( * ) Notice: Subject to any disclaimer, the term of this patent is extended or adjusted under 35 U.S.C. 154(b) by 0 days.

(21) Appl. No.: 15/557,578

(22) PCT Filed: Mar. 30, 2016

(86) PCT No.: PCT/US2016/024912
§ 371 (c)(1),
(2) Date: Sep. 12, 2017

(87) PCT Pub. No.: WO2016/160921
PCT Pub. Date: Oct. 6, 2016

(65) Prior Publication Data
US 2018/0050325 A1  Feb. 22, 2018

Related U.S. Application Data

(60) Provisional application No. 62/140,877, filed on Mar. 31, 2015, provisional application No. 62/242,010, filed on Oct. 15, 2015.

(51) Int. Cl.

| | |
|---|---|
| C07C 29/00 | (2006.01) |
| B01J 23/00 | (2006.01) |
| B01J 21/00 | (2006.01) |
| B01J 37/00 | (2006.01) |
| B01J 23/843 | (2006.01) |
| B01J 23/72 | (2006.01) |
| B01J 37/08 | (2006.01) |
| B01J 37/16 | (2006.01) |
| B01J 21/08 | (2006.01) |
| B01J 35/00 | (2006.01) |
| B01J 35/02 | (2006.01) |
| B01J 35/08 | (2006.01) |
| B01J 35/10 | (2006.01) |
| B01J 37/02 | (2006.01) |
| C07C 29/154 | (2006.01) |
| C07C 29/44 | (2006.01) |
| C07C 29/141 | (2006.01) |

(52) U.S. Cl.
CPC ........... *B01J 23/8437* (2013.01); *B01J 21/08* (2013.01); *B01J 23/72* (2013.01); *B01J 35/0006* (2013.01); *B01J 35/0066* (2013.01); *B01J 35/026* (2013.01); *B01J 35/08* (2013.01); *B01J 35/1038* (2013.01); *B01J 35/1042* (2013.01); *B01J 35/1047* (2013.01); *B01J 37/0018* (2013.01); *B01J 37/0201* (2013.01); *B01J 37/0203* (2013.01); *B01J 37/0236* (2013.01); *B01J 37/088* (2013.01); *B01J 37/16* (2013.01); *C07C 29/141* (2013.01); *C07C 29/154* (2013.01); *C07C 29/44* (2013.01)

(58) Field of Classification Search
CPC ..... C07C 29/141; B01J 23/8437; B01J 21/08; B01J 37/0201; B01J 37/0236; B01J 37/16
See application file for complete search history.

(56) References Cited

U.S. PATENT DOCUMENTS

| | | | |
|---|---|---|---|
| 2,300,969 A | 11/1942 | Reppe et al. | |
| 3,478,112 A | 11/1969 | Adam et al. | |
| 3,920,759 A | 11/1975 | Hort | |
| 4,002,694 A | 1/1977 | Hort | |
| 5,863,856 A | 1/1999 | Mauldin | |
| 6,201,160 B1 | 3/2001 | Brudermuller et al. | |
| 6,689,713 B1 | 2/2004 | Zhao et al. | |
| 2010/0087312 A1 | 4/2010 | Sijpkes et al. | |
| 2011/0082311 A1 | 4/2011 | Soled et al. | |
| 2014/0275639 A1 | 9/2014 | Madon et al. | |

FOREIGN PATENT DOCUMENTS

| | | |
|---|---|---|
| DE | 725326 | 9/1942 |
| WO | WO 2014/128203 A1 | 8/2014 |

OTHER PUBLICATIONS

International Search Report & Written Opinion in International Application No. PCT/US2016/024912, dated Jul. 12, 2016 (18 pages).
Extended European Search Report in EP Application No. 16774065.3, dated Nov. 6, 2018 (9 pages).

*Primary Examiner* — Sikarl A Witherspoon
(74) *Attorney, Agent, or Firm* — Foley & Lardner LLP

(57) ABSTRACT

A process for preparing a catalyst includes impregnating a metal oxide carrier with an aqueous solution to form an impregnated carrier; drying the impregnated carrier to form a dried, impregnated carrier; and heat-treating the dried, impregnated carrier in air to form the catalyst; wherein: the aqueous solution includes a copper salt; and from about 3 wt % to about 15 wt % of a $C_3$-$C_6$ multifunctional carboxylic acid; and the catalyst includes from about 5 wt % to about 50 wt % copper oxide.

20 Claims, 26 Drawing Sheets

Example-1A "0wt% CA"

Example-1A "0wt% CA"

Example-1B "5wt% CA"

Example-1B "5wt% CA"

Example-1C 10wt% CA"

Example-1C "10wt% CA"

Example 2A "0wt% GA"

Example 2A "0wt% GA"

Example 2B "1wt% GA"

Example 2B "1wt% GA"

Example 2C "5wt% GA"

Example 2C "5wt% GA"

Example 2D "7wt% GA"

Example 2D "7wt% GA"

Example 2E "10wt% GA"

Example 2E "10wt% GA"

Example 3A "0wt% MA"

Example 3A "0wt% MA"

Example 3B "2.5wt% MA"

Example 3B "2.5wt% MA"

Example 3C "4.2wt% MA"

Example C "4.2wt% MA"

Example 3D "5.8wt% MA"

Example 3D "5.8wt% MA"

Example 3E "7.5wt% MA"

Example 3E "7.5wt% MA"

Example 4A "0wt% GA"

Example 4A "0wt% GA"

Example 4B "3wt% GA"

Example 4C "5wt% GA"

Example 4D "7wt% GA"

Example 5A "1.5wt% GA"

Example 5A "1.5wt% GA"

Example 5B "2.5wt% GA"

Example 5B "2.5wt% GA"

Example 5C "3.5wt% GA"

Example 5C "3.5wt% GA"

Example D "5.0wt% GA"

Example 5D "5.0wt% GA"

Example 5E "7.0wt% GA"

Example 5E "7.0wt% GA"

HYDROGENATION AND ETHYNYLATION CATALYSTS

CROSS-REFERENCE TO RELATED APPLICATIONS

This application is a U.S. National Phase Application under 35 U.S.C. § 371 of International Application No. PCT/US2016/024912, filed on Mar. 30, 2016, which claims priority to U.S. Provisional Application Nos. 62/140,877, filed Mar. 31, 2015, and 62/242,010, filed Oct. 15, 2015, the entire contents of which are incorporated herein by reference in their entireties.

FIELD

The present technology is generally related to catalysts. More specifically, the technology is related to hydrogenation, dehydrogenation, ethynylation, and hydrogenolysis catalysts.

SUMMARY

In one aspect, a process is provided for the ethynylation of formaldehyde to make 1,4 butynediol. The process uses a catalyst prepared by impregnating a metal oxide carrier with a copper salt solution, and optionally a bismuth salt, containing from 3 wt % up to 15 wt % of at least one multifunctional carboxylic acid having from about 3 to 6 carbon atoms to form an impregnated carrier, drying the impregnated carrier, and calcining the impregnated carrier, where the catalyst contains from about 5 wt % to about 40 wt % copper oxide.

In another aspect, a process is provided for forming a catalyst for hydrogenation, dehydrogenation, or hydrogenolysis, the process including impregnating a metal oxide carrier with an aqueous solution to form an impregnated carrier; drying the impregnated carrier to form a dried, impregnated carrier; and heat-treating the dried, impregnated carrier in air to form the catalyst. The aqueous solution of the method includes a copper salt; and from about 1 wt % to about 15 wt % of a $C_3$-$C_6$ multifunctional carboxylic acid; and the catalyst includes from about 5 wt % to about 40 wt % copper oxide. In some embodiments, the impregnating is carried out until incipient wetness is achieved. Where the catalyst is a hydrogenation catalyst, in some embodiments, the aqueous solution consists essentially of the copper salt, from about 1 wt % to about 15 wt % of a $C_3$-$C_6$ multifunctional carboxylic acid, and, optionally, a precipitation agent.

In some embodiments, the heat-treating includes calcining in air. In other embodiments, the heat-treating includes pyrolyzing. In other embodiments, the heat-treating includes calcining in an oxygen-limited atmosphere.

In another aspect, an ethynylation catalyst prepared according to any of the methods described herein is provided.

In another aspect, a process is provided for the synthesis of butynediol. The process may include contacting formaldehyde and acetylene under ethynylation conditions with any of the ethynylation catalysts described or prepared herein. The process may include activating the ethynylation catalyst by forming Cu(I)acetylide.

In another aspect, a hydrogenation catalyst prepared according to any of the methods described herein is provided.

In another aspect, a process is provided for the hydrogenation of aldehydes and ketones to alcohols, dehydrogenating alcohols to aldehydes and ketones, or hydrogenolysis of esters to alcohols under reducing conditions with any of the catalysts described or prepared herein. In one aspect, a process is provided for the hydrogenation of butyraldehyde to butanol under hydrogenation conditions with any of the catalysts described or prepared herein.

DETAILED DESCRIPTION

Figure 1:
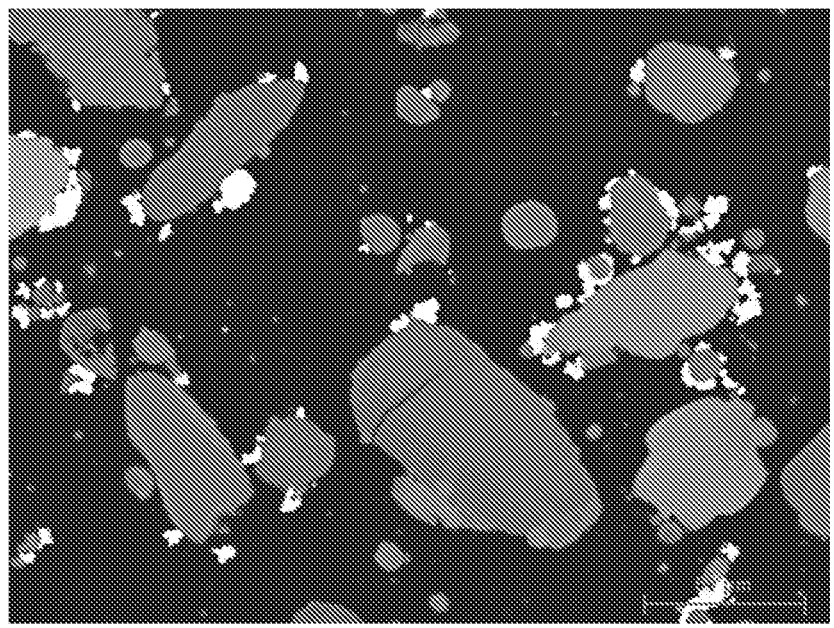
FIG. 1 is a high magnification image of Example-1A "0 wt % Citric Acid" catalyst using Scanning Electron Microscopy, according to the examples.
Figure 2:
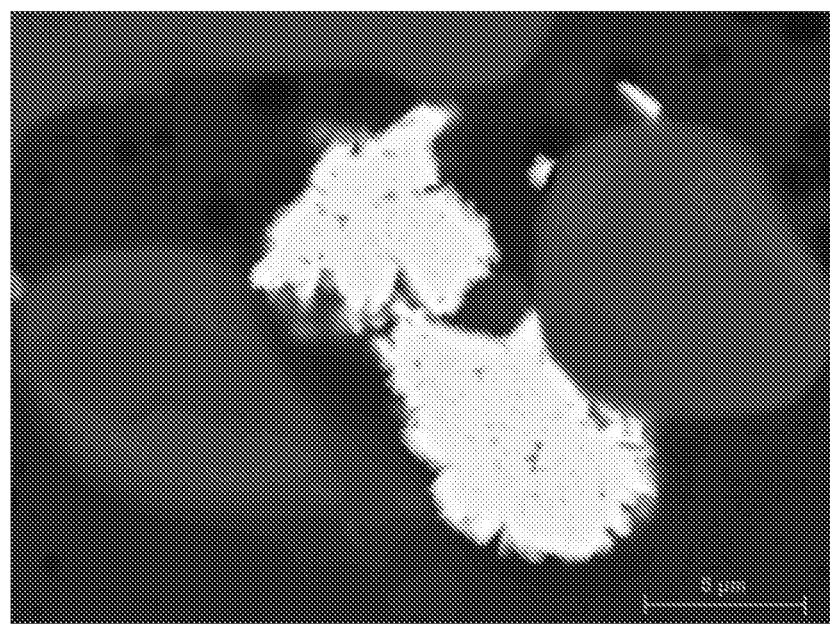
FIG. 2 is a lower magnification image of Example-1A "0 wt % Citric Acid" catalyst using Scanning Electron Microscopy, according to the examples.
Figure 3:
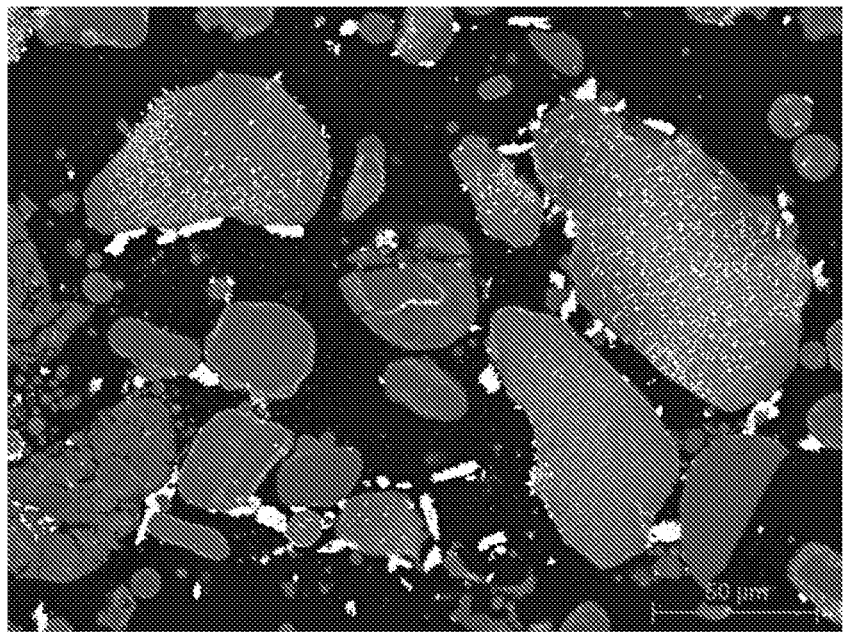
FIG. 3 is a high magnification image of Example-1B "5 wt % Citric Acid" catalyst using Scanning Electron Microscopy, according to the examples.
Figure 4:
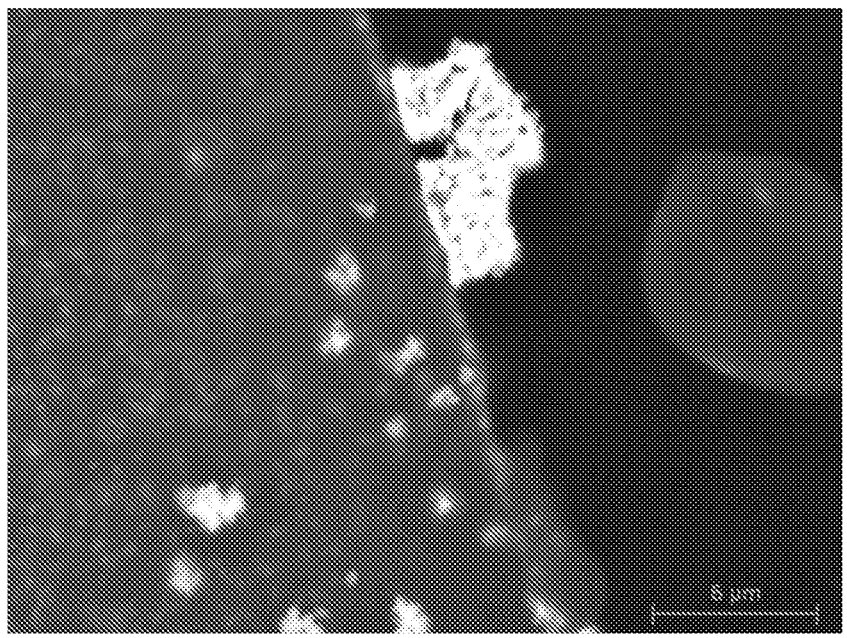
FIG. 4 is a lower magnification image of Example-1B "5 wt % Citric Acid" catalyst using Scanning Electron Microscopy, according to the examples.
Figure 5:
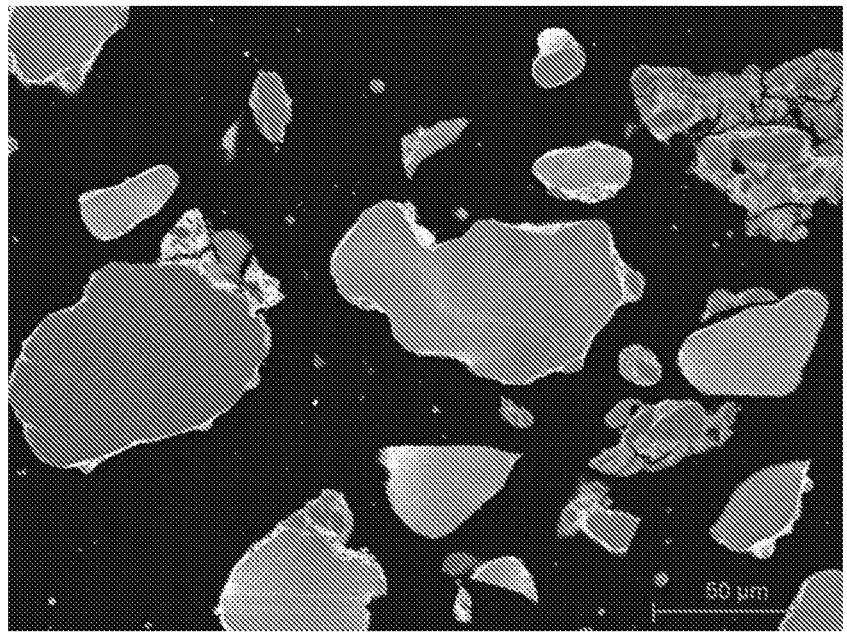
FIG. 5 is a high magnification image of Example-1C "10 wt % Citric Acid" catalyst using Scanning Electron Microscopy, according to the examples.
Figure 6:
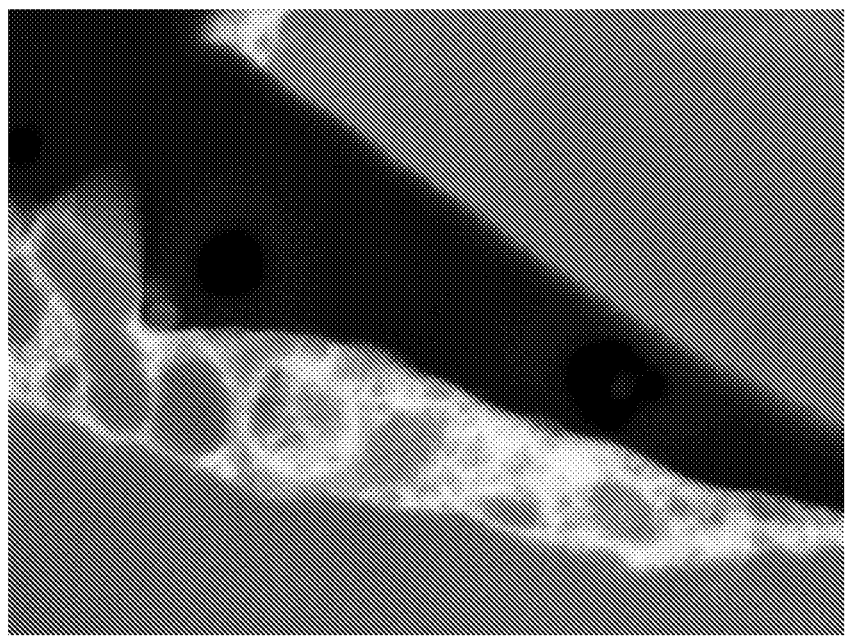
FIG. 6 is a lower magnification image of Example-1C "10 wt % Citric Acid" catalyst using Scanning Electron Microscopy, according to the examples.
Figure 7:
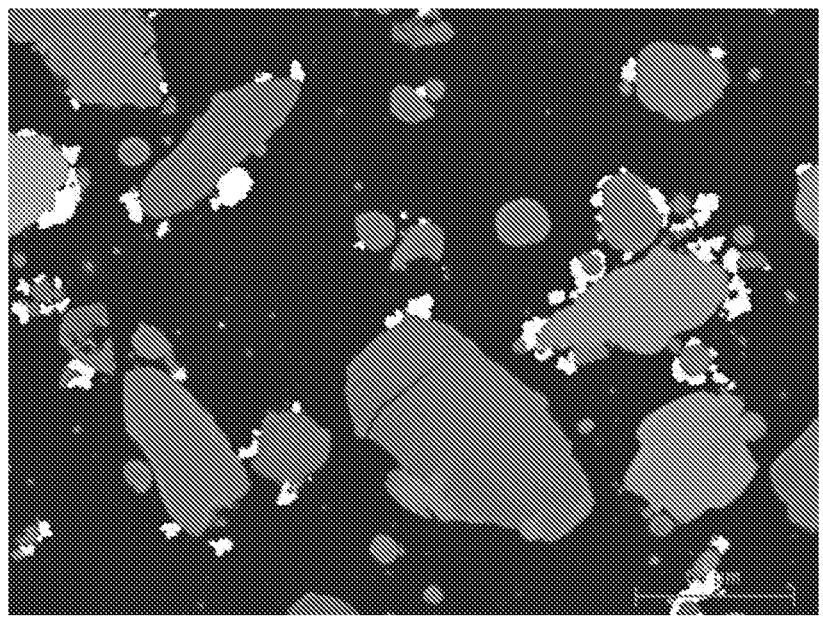
FIG. 7 is a high magnification image of Example-2A "0 wt % Glutaric Acid" catalyst using Scanning Electron Microscopy, according to the examples.
Figure 8:
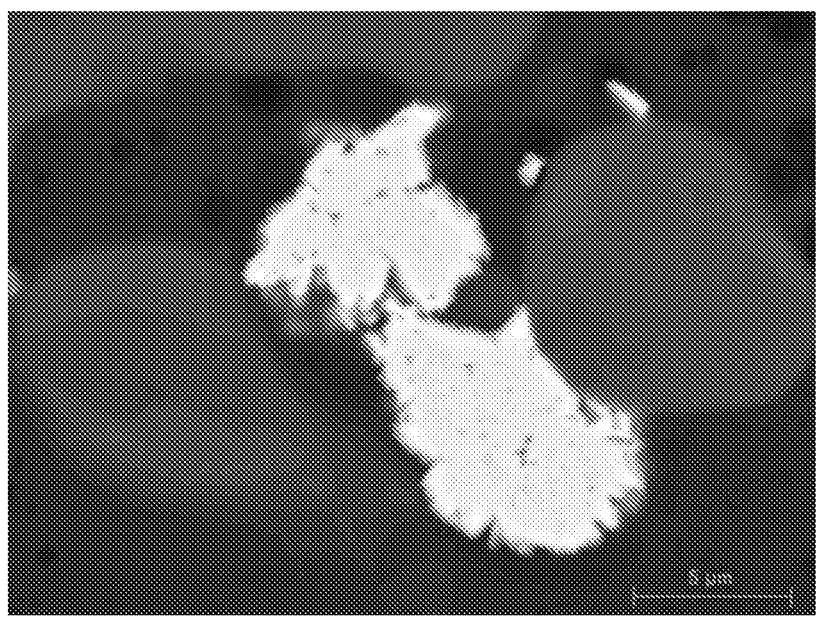
FIG. 8 is a lower magnification image of Example-2A "0 wt % Glutaric Acid" catalyst using Scanning Electron Microscopy, according to the examples.
Figure 9:
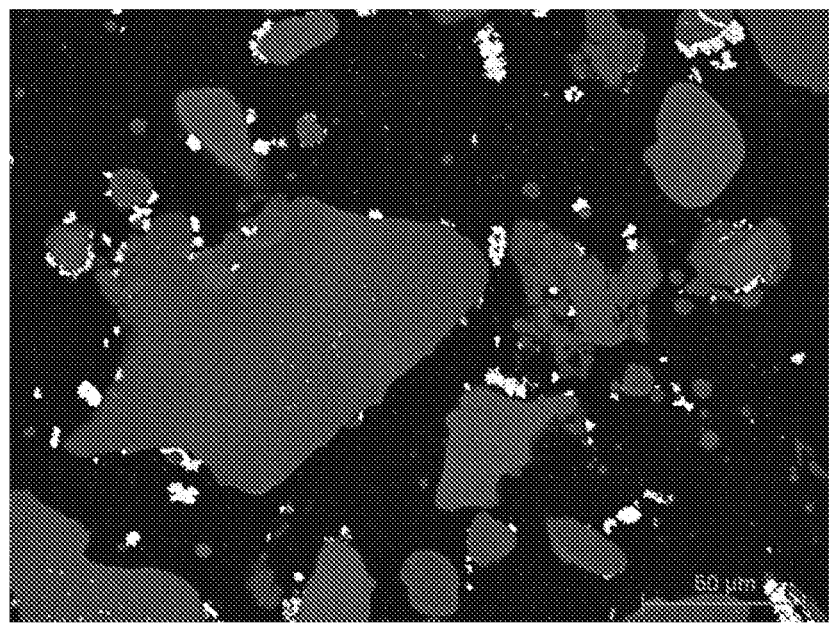
FIG. 9 is a high magnification image of Example-2B "1 wt % Glutaric Acid" catalyst using Scanning Electron Microscopy, according to the examples.
Figure 10:
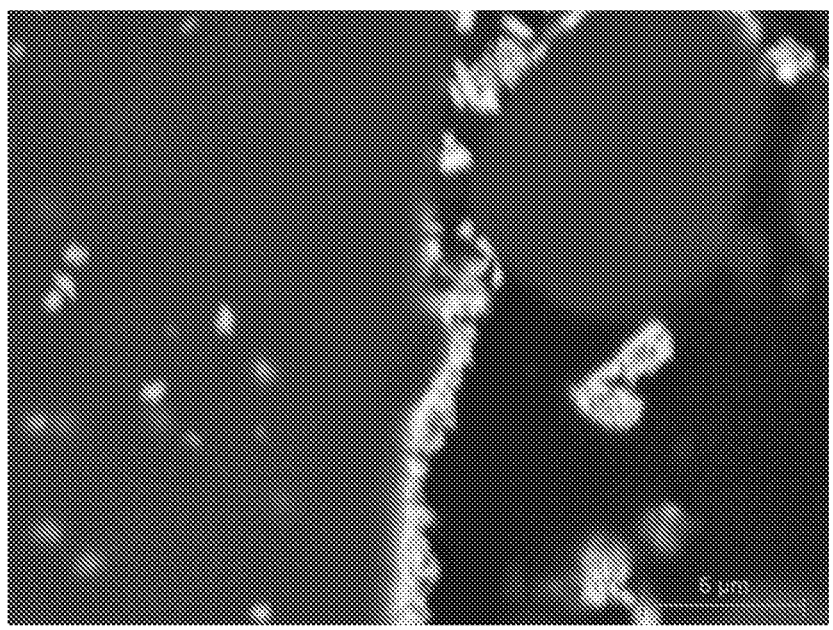
FIG. 10 is a lower magnification image of Example-2B "1 wt % Glutaric Acid" catalyst using Scanning Electron Microscopy, according to the examples.
Figure 11:
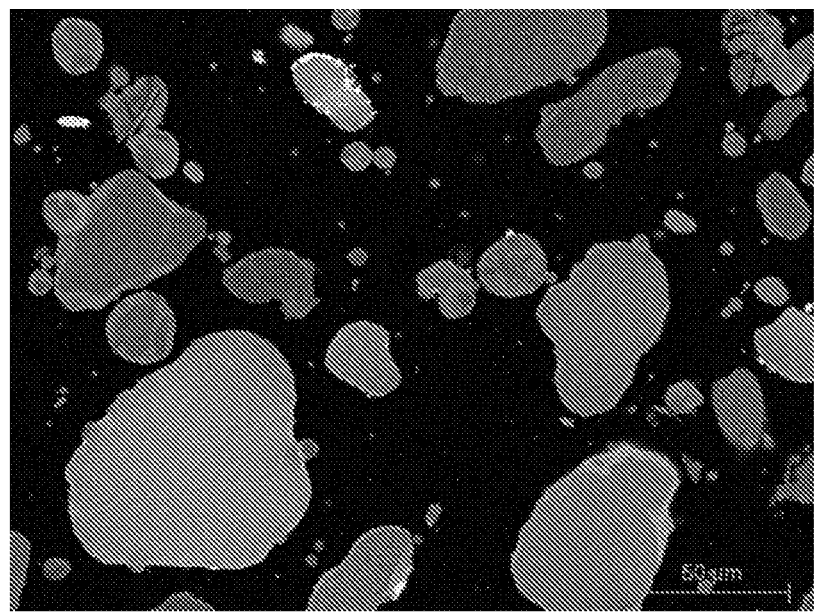
FIG. 11 is a high magnification image of Example-2C "5 wt % Glutaric Acid" catalyst using Scanning Electron Microscopy, according to the examples.
Figure 12:
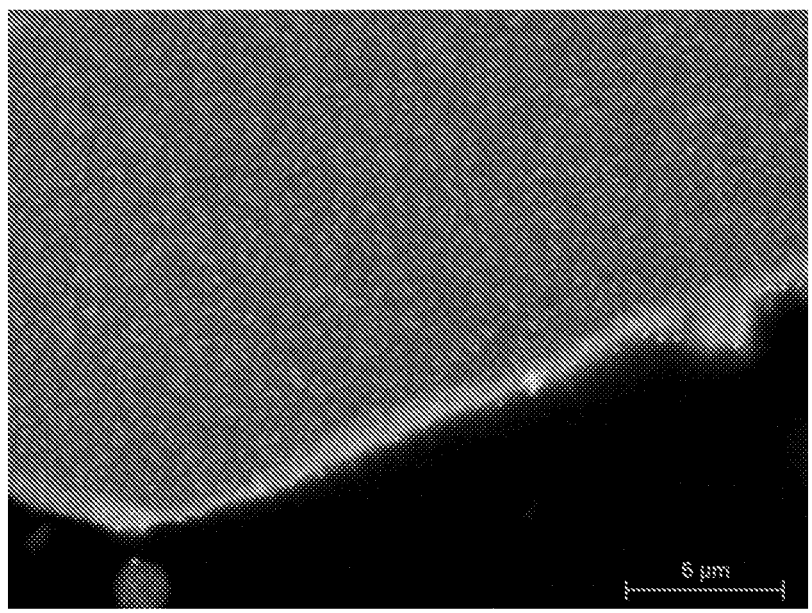
FIG. 12 is a lower magnification image of Example-2B "5 wt % Glutaric Acid" catalyst using Scanning Electron Microscopy, according to the examples.
Figure 13:
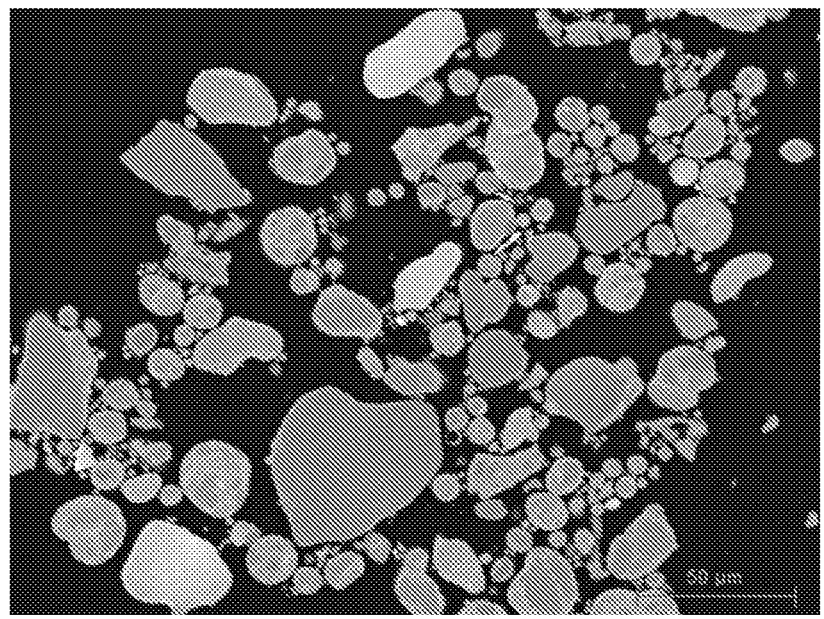
FIG. 13 is a high magnification image of Example-2D "7 wt % Glutaric Acid" catalyst using Scanning Electron Microscopy, according to the examples.
Figure 14:
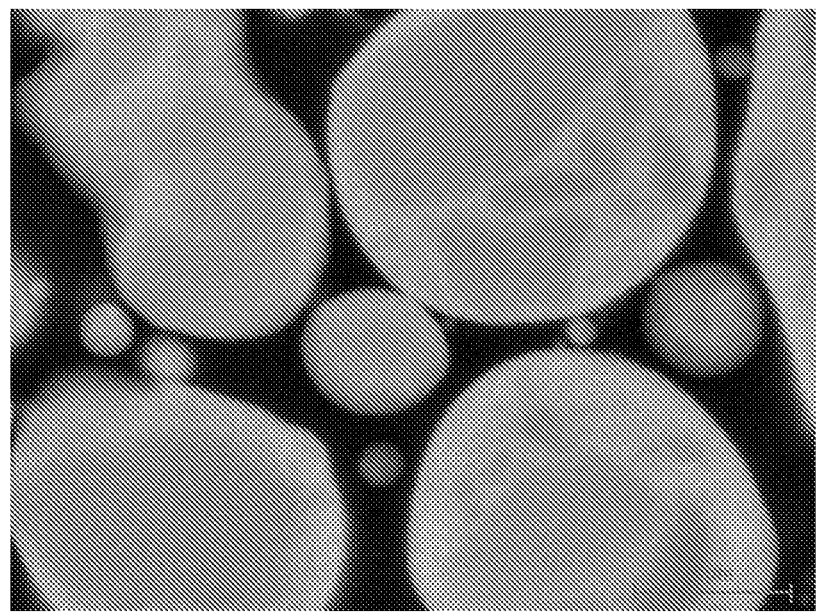
FIG. 14 is a lower magnification image of Example-2D "7 wt % Glutaric Acid" catalyst using Scanning Electron Microscopy, according to the examples.
Figure 15:
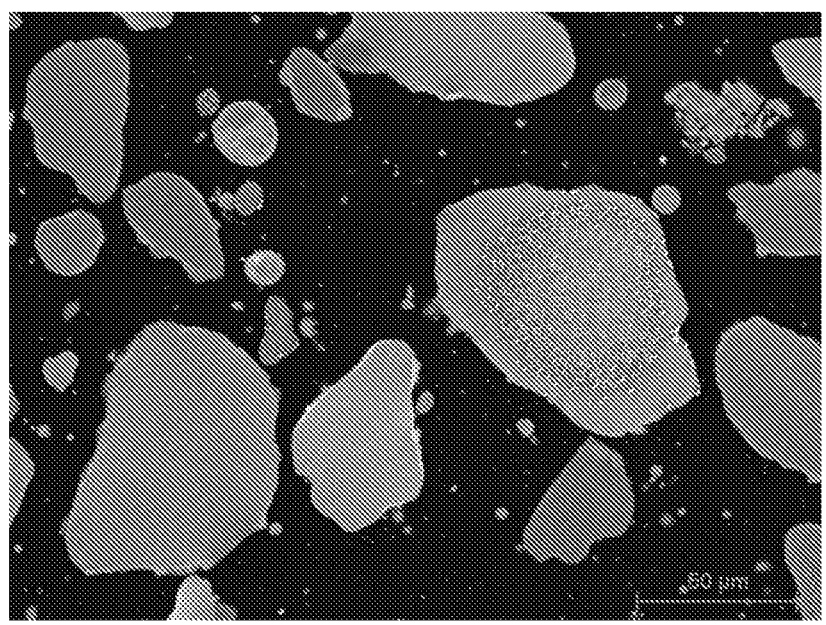
FIG. 15 is a high magnification image of Example-2E "10 wt % Glutaric Acid" catalyst using Scanning Electron Microscopy, according to the examples.
Figure 16:
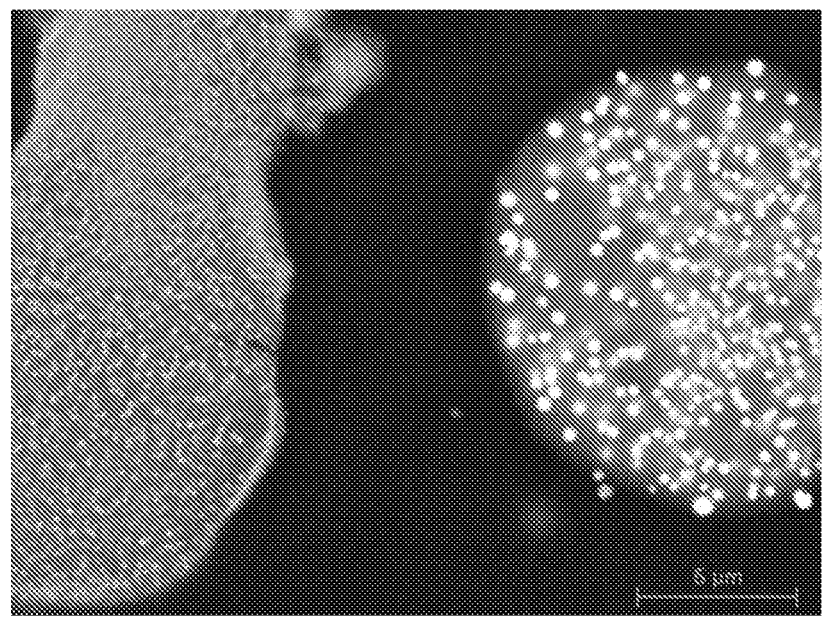
FIG. 16 is a lower magnification image of Example-2E "10 wt % Glutaric Acid" catalyst using Scanning Electron Microscopy, according to the examples.
Figure 17:
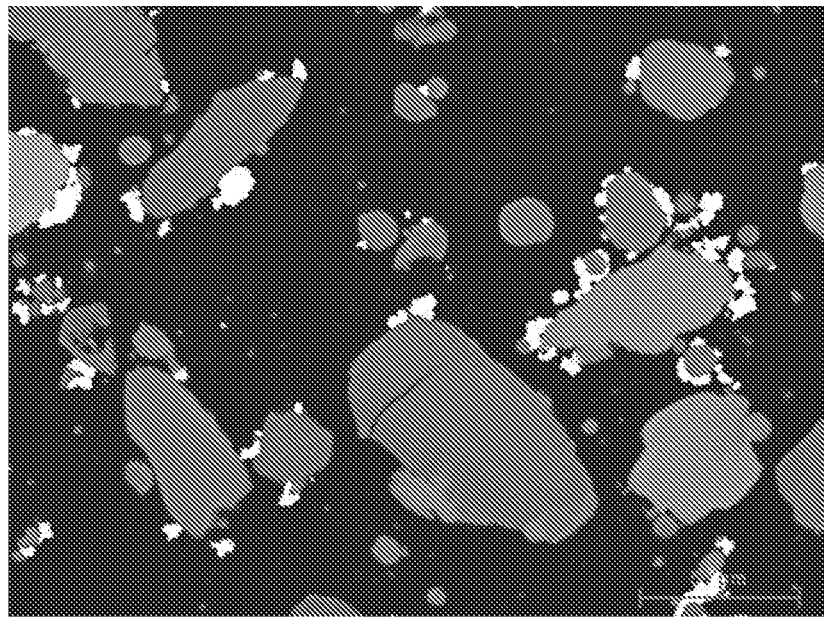
FIG. 17 is a high magnification image of Example-3A "0 wt % Malonic Acid" catalyst using Scanning Electron Microscopy, according to the examples.
Figure 18:
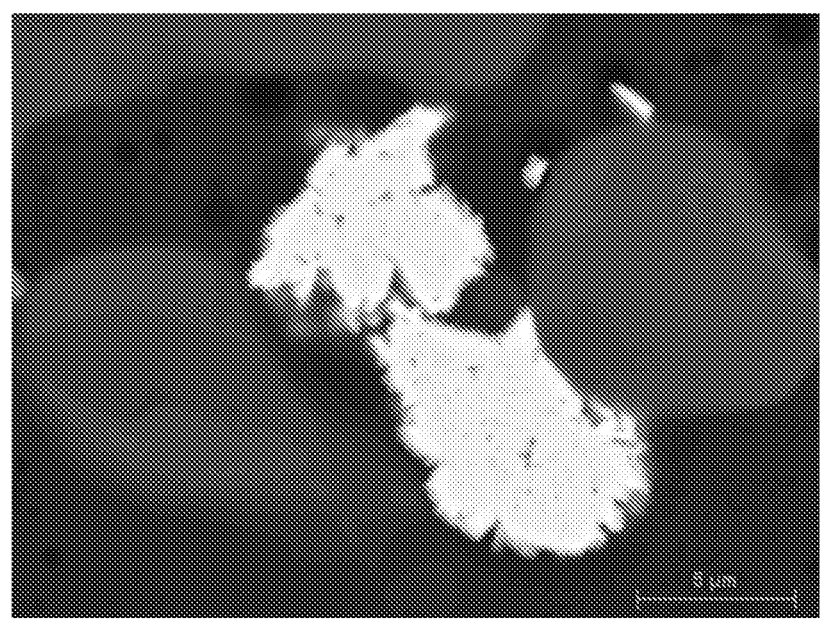
FIG. 18 is a lower magnification image of Example-3A "0 wt % Malonic Acid" catalyst using Scanning Electron Microscopy, according to the examples.
Figure 19:
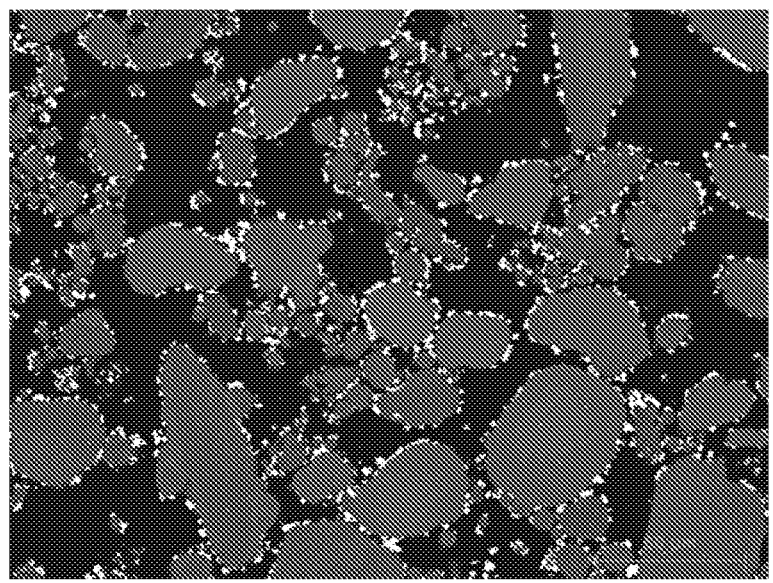
FIG. 19 is a high magnification image of Example-3B "2.5 wt % Malonic Acid" catalyst using Scanning Electron Microscopy, according to the examples.
Figure 20:
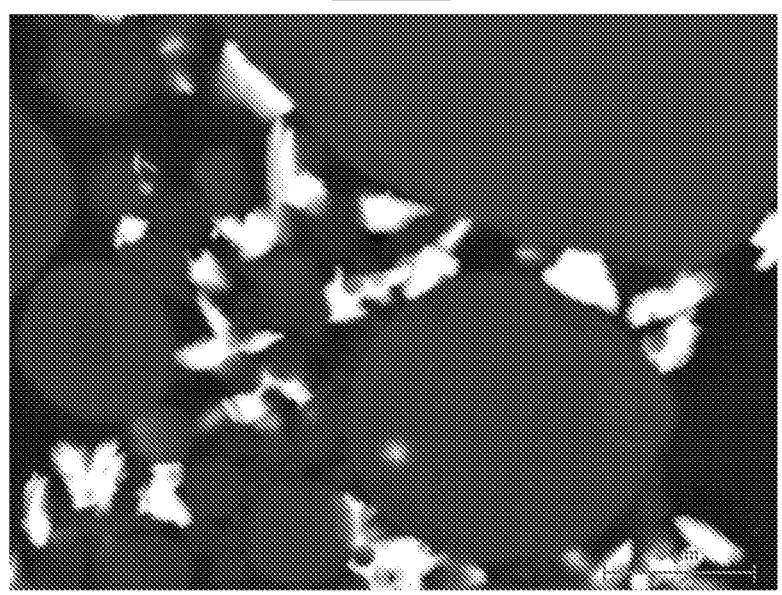
FIG. 20 is a lower magnification image of Example-3B "2.5 wt % Malonic Acid" catalyst using Scanning Electron Microscopy, according to the examples.
Figure 21:
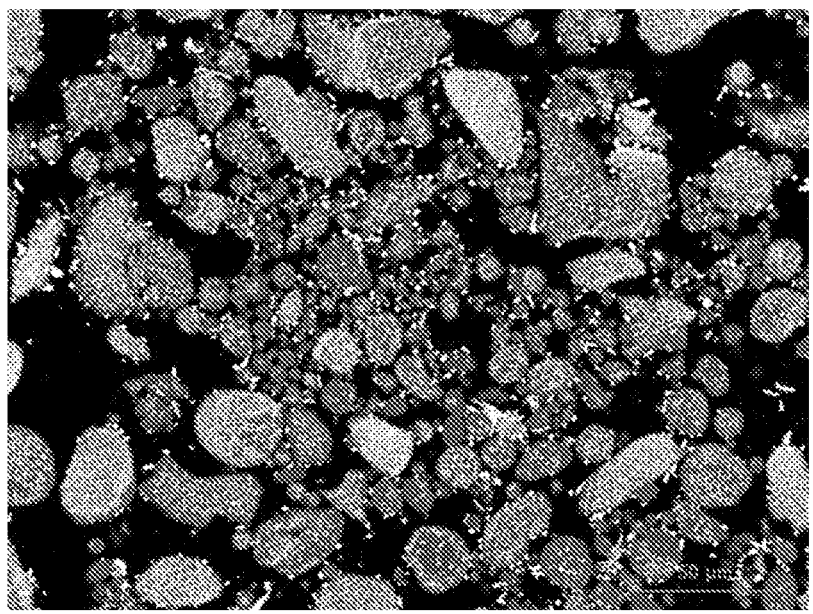
FIG. 21 is a high magnification image of Example-3C "4.2 wt % Malonic Acid" catalyst using Scanning Electron Microscopy, according to the examples.
Figure 22:
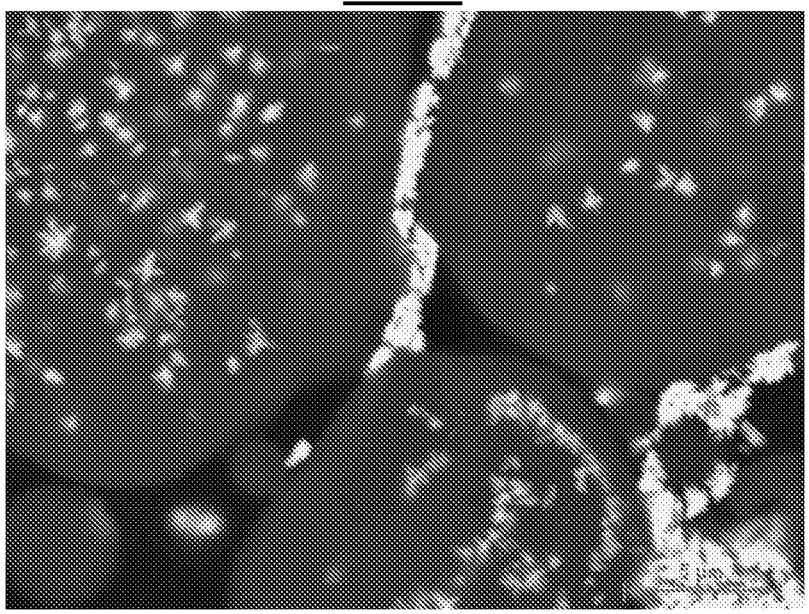
FIG. 22 is a lower magnification image of Example-3C "4.2 wt % Malonic Acid" catalyst using Scanning Electron Microscopy, according to the examples.
Figure 23:
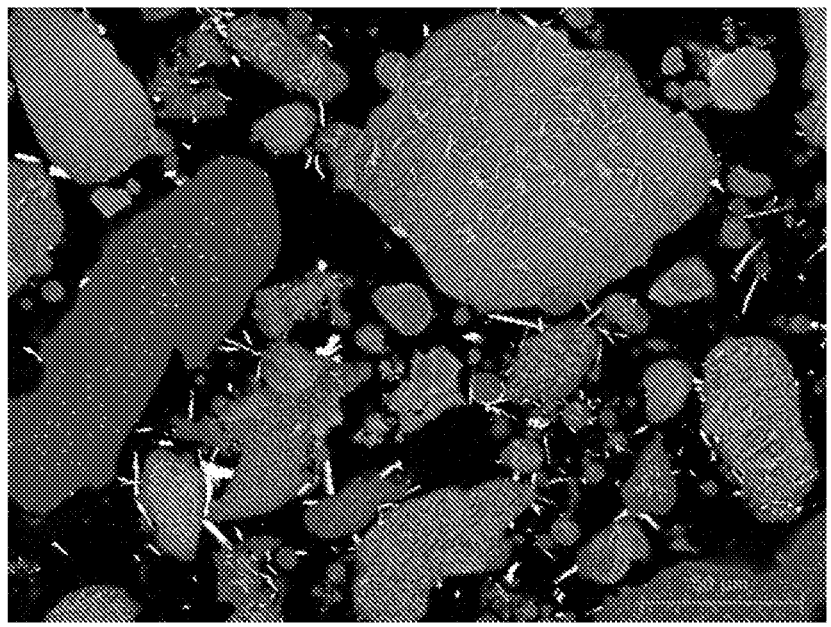
FIG. 23 is a high magnification image of Example-3D "5.8 wt % Malonic Acid" catalyst using Scanning Electron Microscopy, according to the examples.
Figure 24:
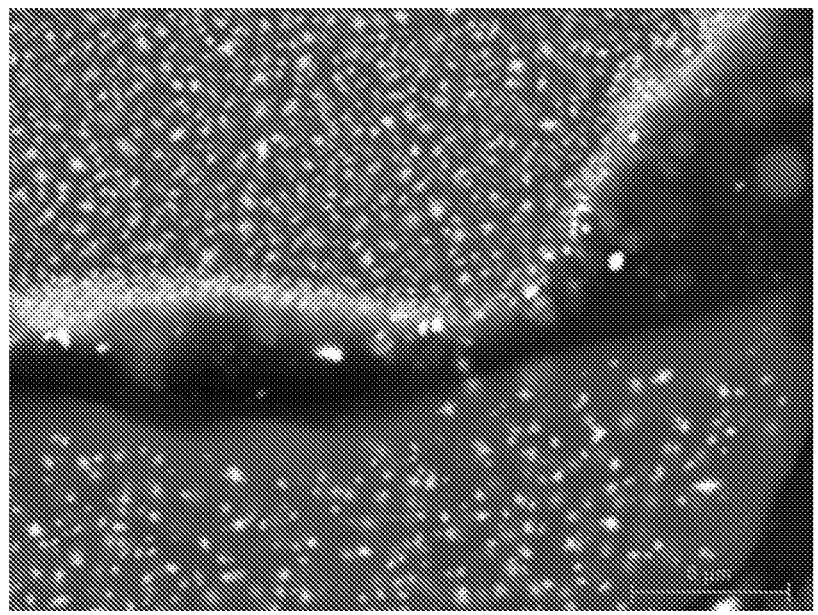
FIG. 24 is a lower magnification image of Example-3D "5.8 wt % Malonic Acid" catalyst using Scanning Electron Microscopy, according to the examples.
Figure 25:
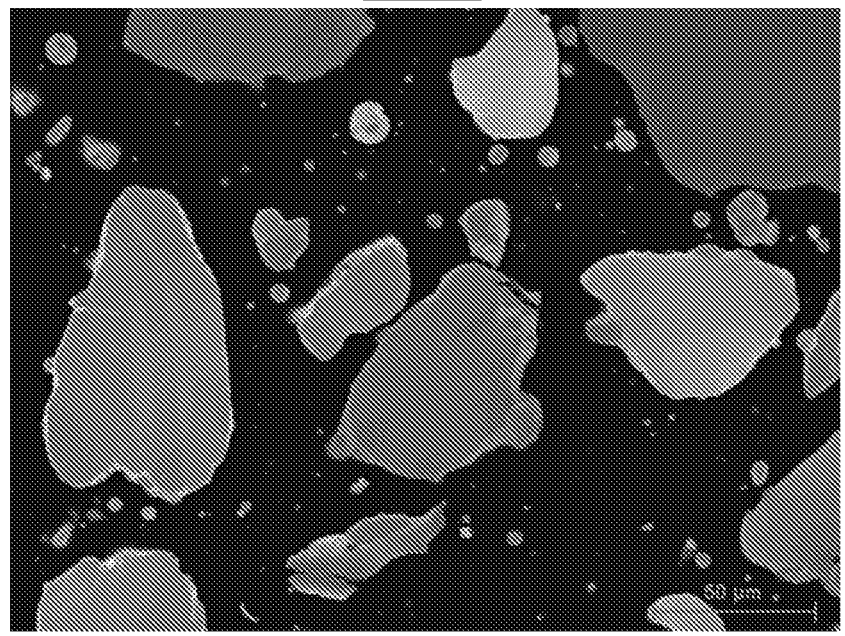
FIG. 25 is a high magnification image of Example-3E "7.5 wt % Malonic Acid" catalyst using Scanning Electron Microscopy, according to the examples.
Figure 26:
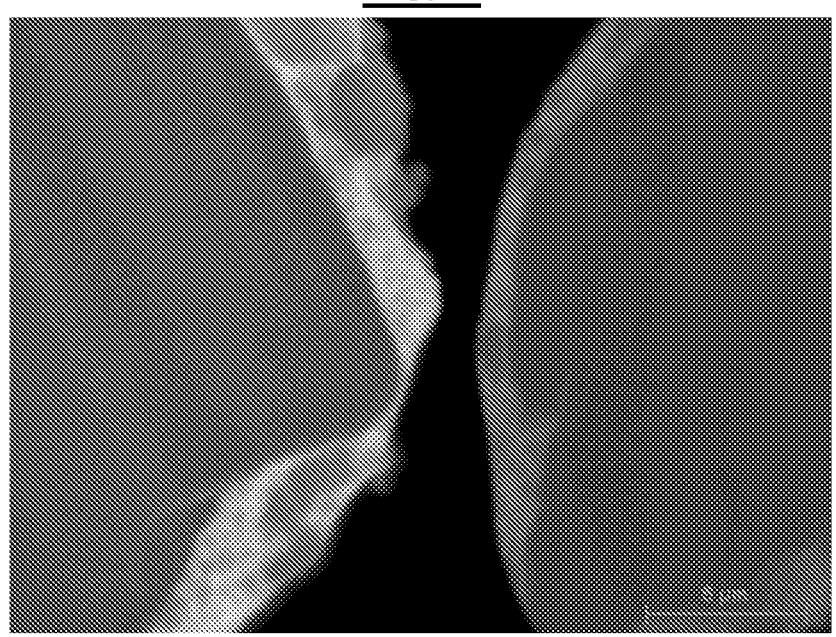
FIG. 26 is a lower magnification image of Example-3E "7.5 wt % Malonic Acid" catalyst using Scanning Electron Microscopy, according to the examples.
Figure 27:
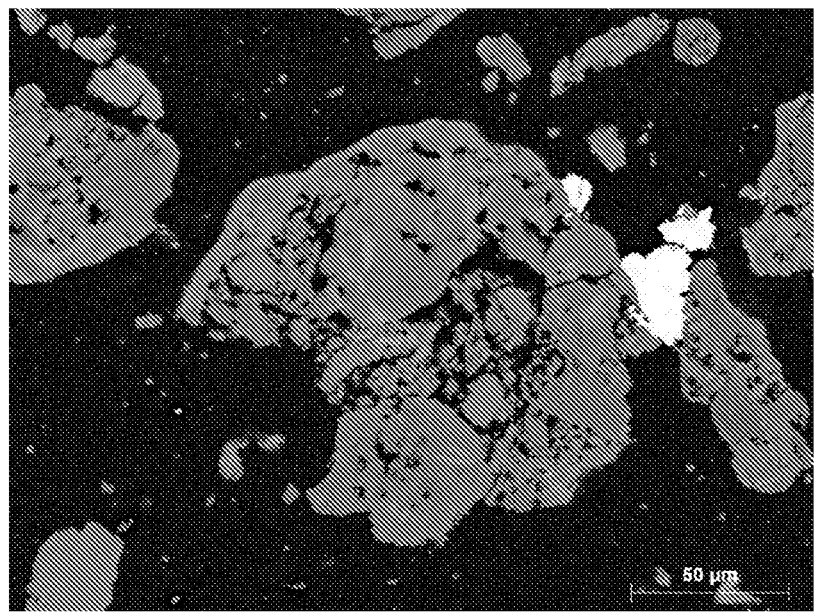
FIG. 27 is a high magnification image of Example-4A "0 wt % Glutaric Acid" catalyst using Scanning Electron Microscopy, according to the examples.
Figure 28:
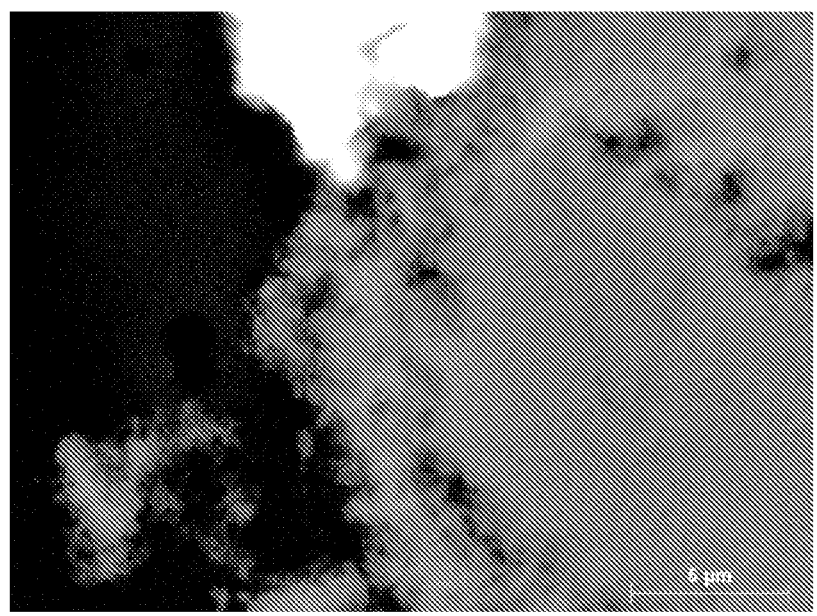
FIG. 28 is a lower magnification image of Example-4A "0 wt % Glutaric Acid" catalyst using Scanning Electron Microscopy, according to the examples.
Figure 29:
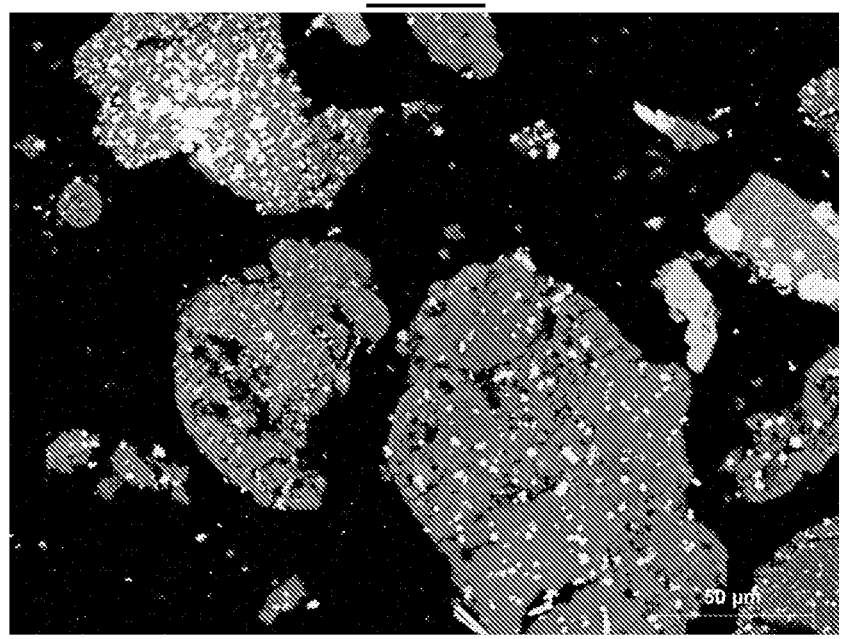
FIG. 29 is a high magnification image of Example-4B "3 wt % Glutaric Acid" catalyst using Scanning Electron Microscopy, according to the examples.
Figure 30:
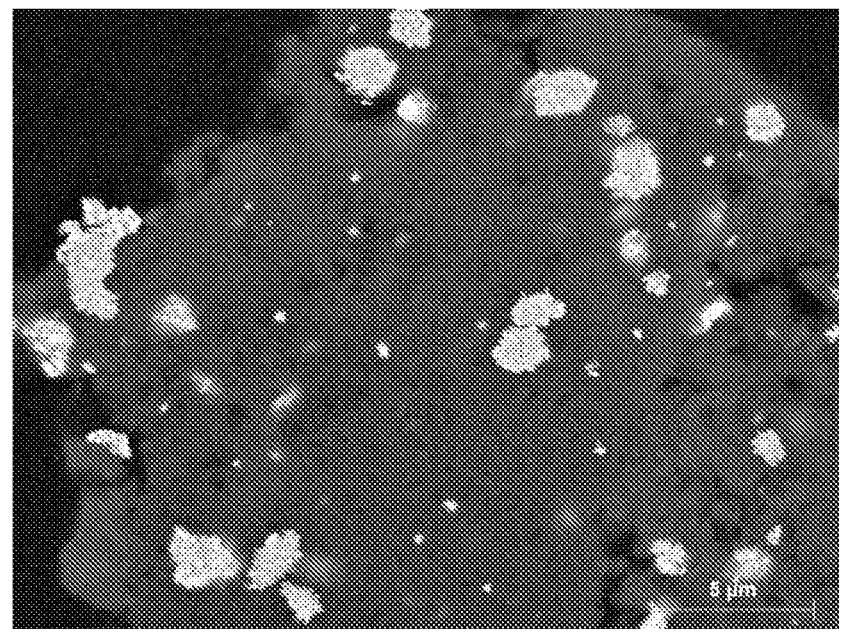
FIG. 30 is a lower magnification image of Example-4B "3 wt % Glutaric Acid" catalyst using Scanning Electron Microscopy, according to the examples.
Figure 31:
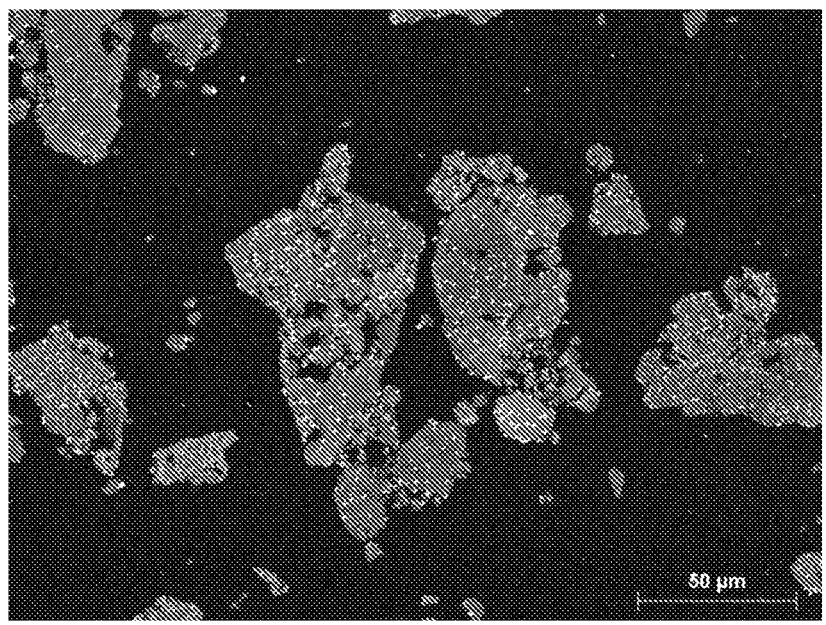
FIG. 31 is a high magnification image of Example-4C "5 wt % Glutaric Acid" catalyst using Scanning Electron Microscopy, according to the examples.
Figure 32:
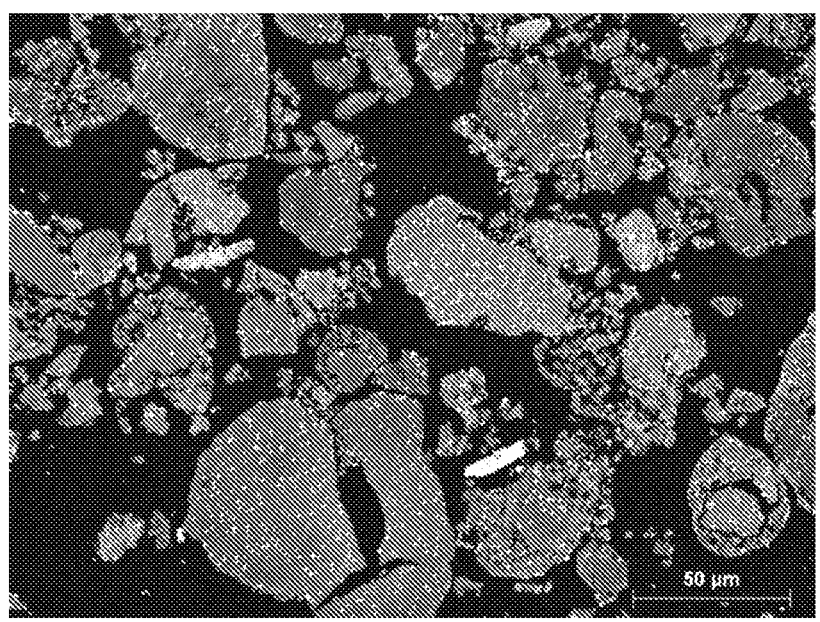
FIG. 32 is a high magnification image of Example-4D "7 wt % Glutaric Acid" catalyst using Scanning Electron Microscopy, according to the examples.
Figure 33:
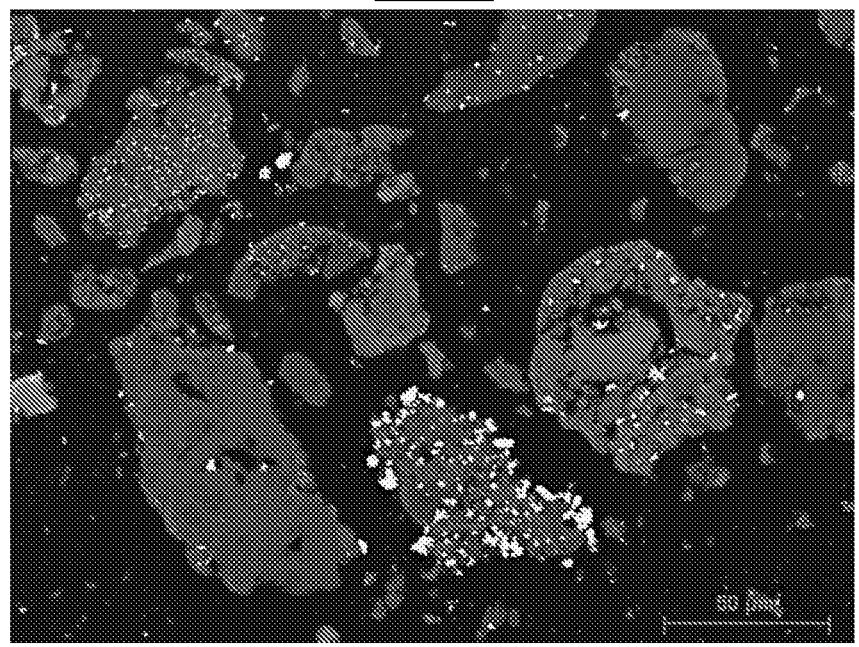
FIG. 33 is a high magnification image of Example-5A "1.5 wt % Glutaric Acid" catalyst using Scanning Electron Microscopy, according to the examples.
Figure 34:
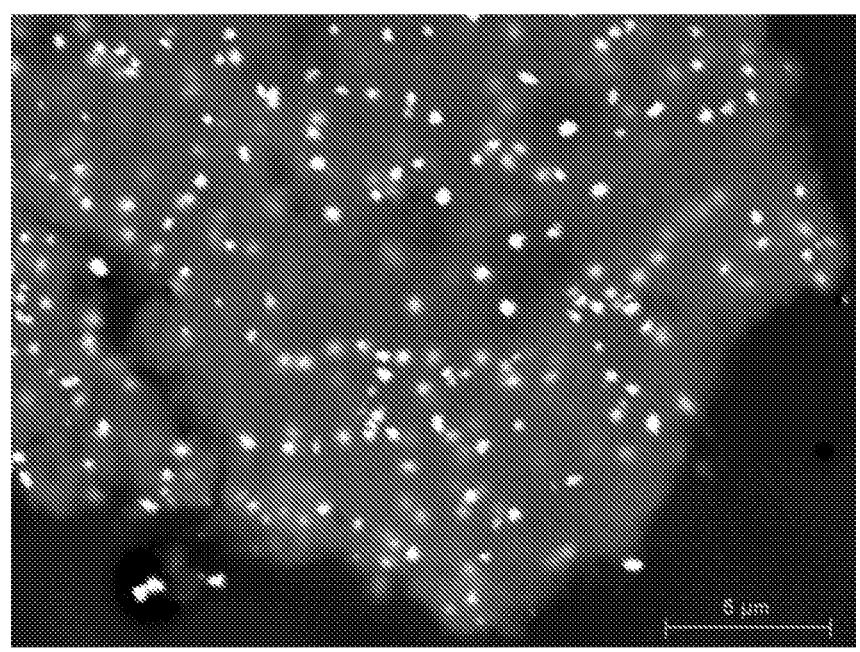
FIG. 34 is a lower magnification image of Example-5A "1.5 wt % Glutaric Acid" catalyst using Scanning Electron Microscopy, according to the examples.
Figure 35:
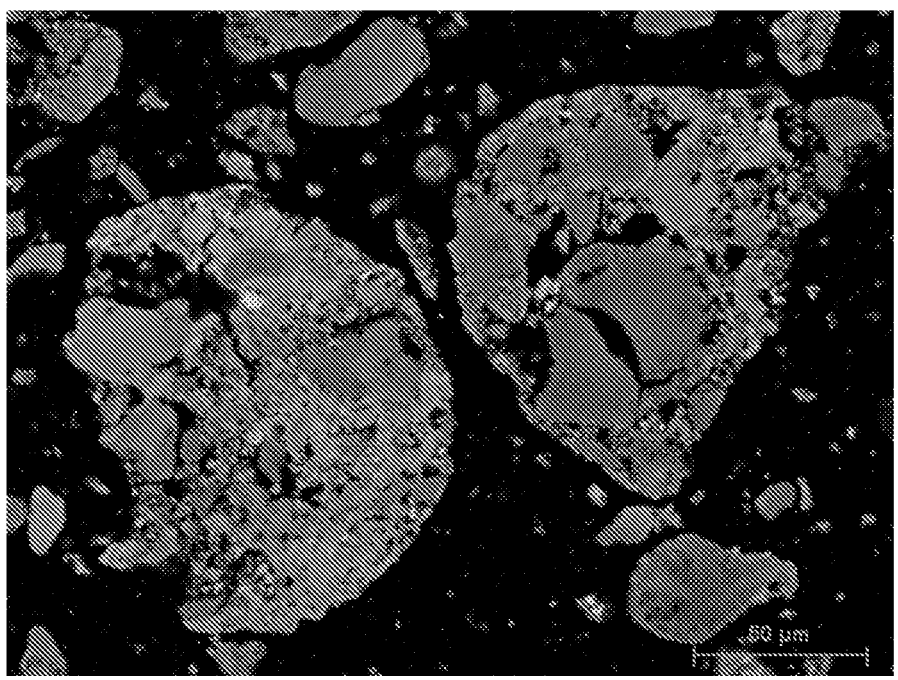
FIG. 35 is a high magnification image of Example-5B "2.5 wt % Glutaric Acid" catalyst using Scanning Electron Microscopy, according to the examples.
Figure 36:
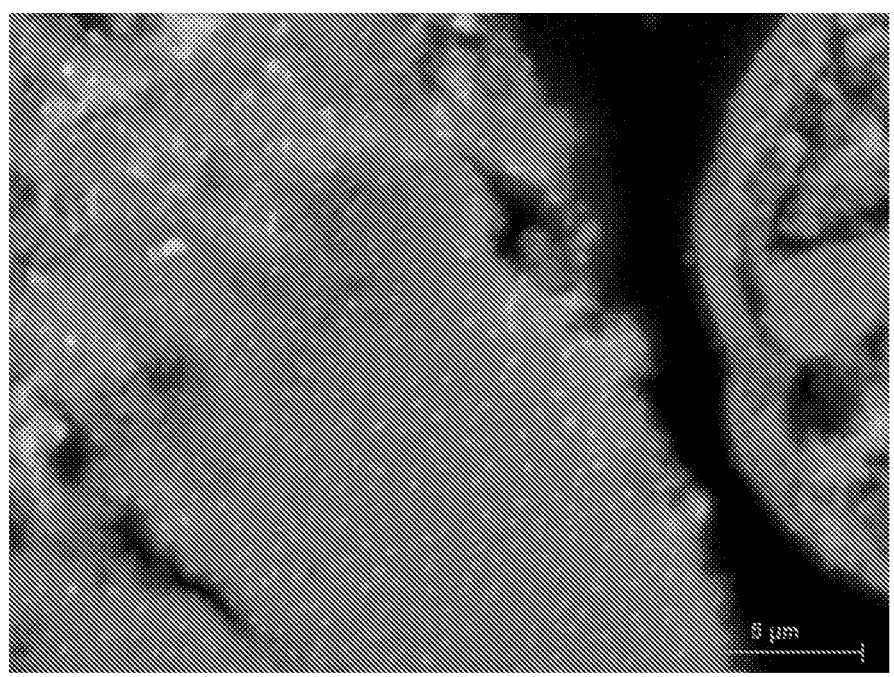
FIG. 36 is a lower magnification image of Example-5B "2.5 wt % Glutaric Acid" catalyst using Scanning Electron Microscopy, according to the examples.
Figure 37:
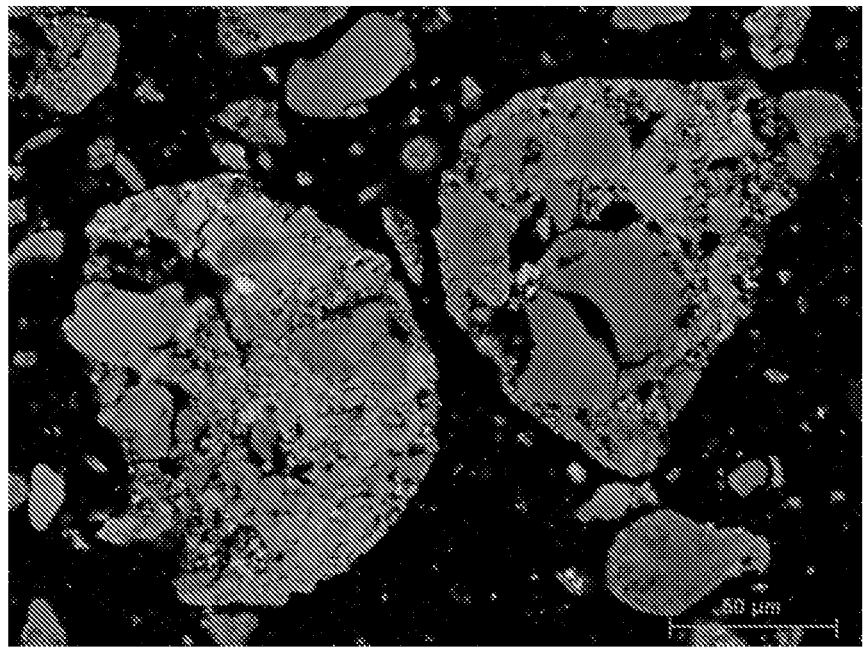
FIG. 37 is a high magnification image of Example-5C "3.5 wt % Glutaric Acid" catalyst using Scanning Electron Microscopy, according to the examples.
Figure 38:
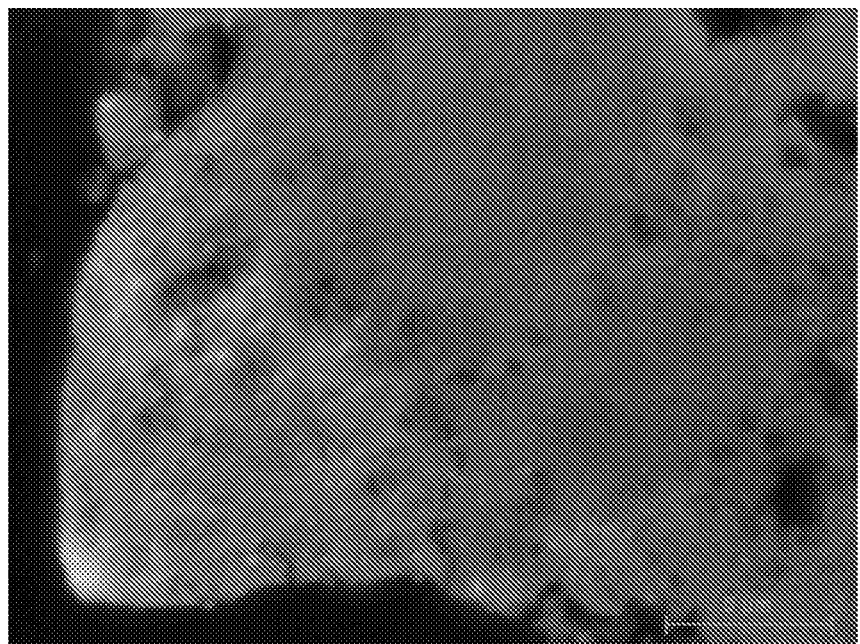
FIG. 38 is a lower magnification image of Example-5C "3.5 wt % Glutaric Acid" catalyst using Scanning Electron Microscopy, according to the examples.
Figure 39:
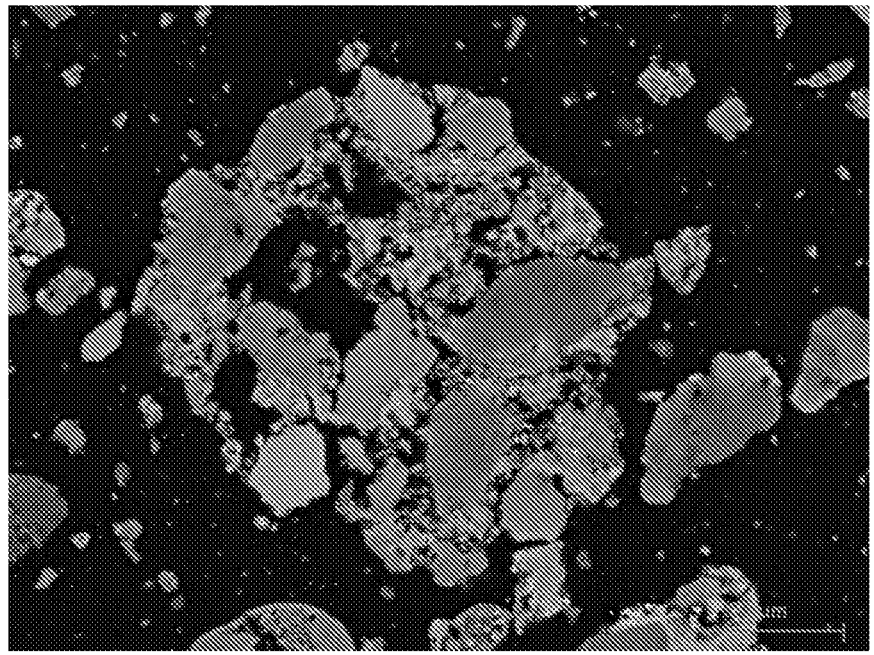
FIG. 39 is a high magnification image of Example-5D "5.0 wt % Glutaric Acid" catalyst using Scanning Electron Microscopy, according to the examples.
Figure 40:
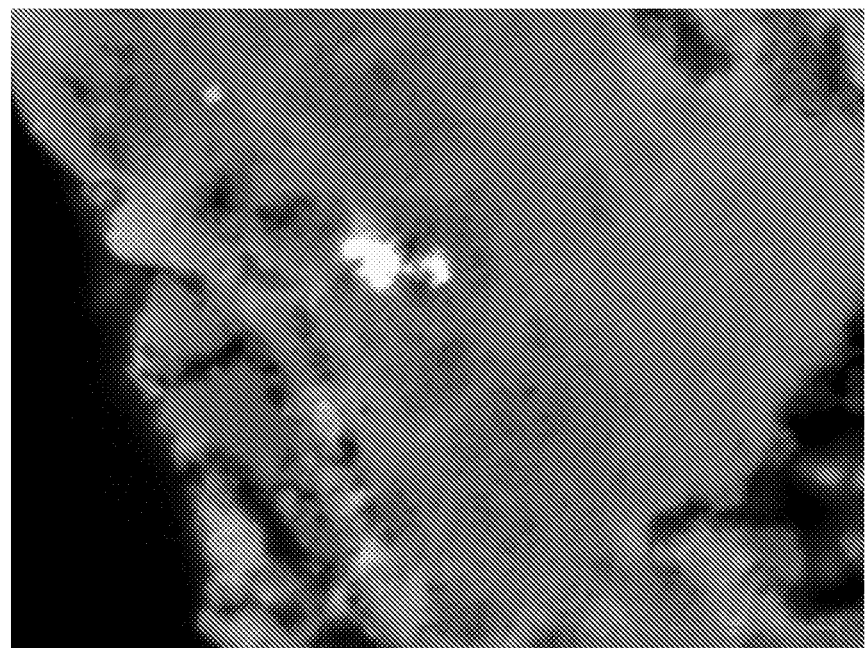
FIG. 40 is a lower magnification image of Example-5D "5.0 wt % Glutaric Acid" catalyst using Scanning Electron Microscopy, according to the examples.
Figure 41:
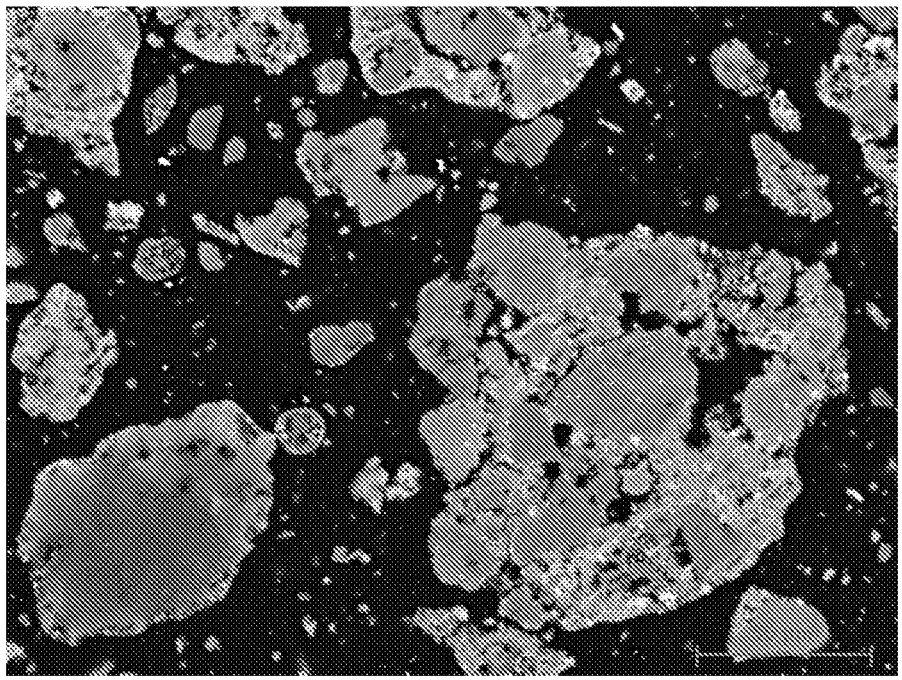
FIG. 41 is a high magnification image of Example-5E "7.0 wt % Glutaric Acid" catalyst using Scanning Electron Microscopy, according to the examples.
Figure 42:
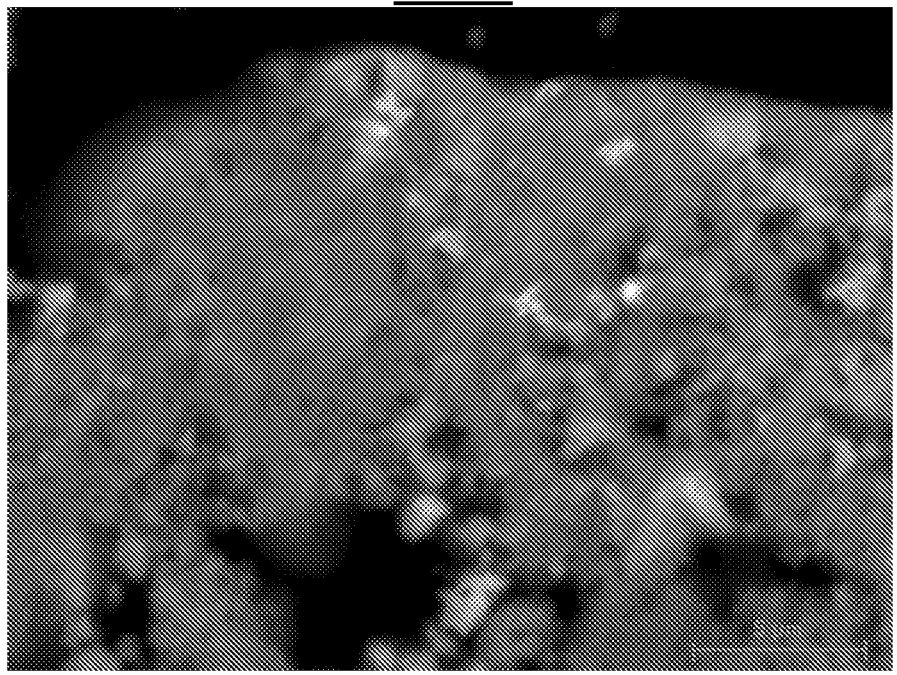
FIG. 42 is a lower magnification image of Example-5E "7.0 wt % Glutaric Acid" catalyst using Scanning Electron Microscopy, according to the examples.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s).

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

The use of the terms "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

In one aspect, a process is provided for the preparation of hydrogenation, dehydrogenation, ethynylation, or hydrogenolysis catalysts. The catalysts may be used in a variety of processes, including the hydrogenation aldehydes, ketones and esters alcohols. In some embodiments, the process provides for the preparation of hydrogenation catalysts. For example, in one embodiment the conversion of butyraldehyde to butanol, or the ethynylation of formaldehyde to 1,4 butynediol (i.e. the "Reppe Process").

The process uses a catalyst prepared by impregnating a metal oxide carrier with an aqueous copper salt solution, and optionally a bismuth salt, containing from about 1 to about 15 wt % of at least one multifunctional carboxylic acid having from about 3 to 6 carbon atoms to form an impregnated carrier, drying the impregnated carrier to form a dried impregnated carrier, and heat-treating the dried impregnated carrier to form the catalyst, where the catalyst contains from about 5 wt % to about 50 wt % copper oxide. In some embodiments, from about 3 to about 15 wt % of at least one multifunctional carboxylic acid are employed, and the catalyst contains from about 5 wt % to about 40 wt % copper oxide. The heat-treating may include calcination or pyrolysis as described vide infra.

In forming the catalyst, a metal oxide carrier is impregnated with an aqueous copper salt solution, and the solution may optionally also contain a bismuth salt. The metal oxide carrier is typically a particulate material having an average particle diameter from about 5 µm to about 100 µm. In some embodiments, the particulate material has an average particle diameter from about 10 µm to 40 µm.

The aqueous copper salt solution also contains at least one multifunctional carboxylic acid having from about 3 to 6 carbon atoms. In some embodiments, the aqueous copper salt solution may contain from about 1 wt % to about 15 wt % of the multifunctional carboxylic acid. In some embodiments, the aqueous copper salt solution may contain from about 3 wt % to about 15 wt % of the multifunctional carboxylic acid. The metal:carboxylic acid ratio on a molar basis may be from about 1 to about 15, or from about 5 to about 9. Illustrative copper salts include, but are not limited to, copper sulfate, copper nitrate, copper acetate, copper chloride, and copper citrate. In some embodiments, the copper salt is $Cu(NO_3)_2$. Illustrative bismuth salts include, but are not limited to, bismuth nitrate, bismuth chloride, bismuth citrate, bismuth sulfate, and bismuth acetate. In some embodiments, the bismuth salt is $Bi(NO_3)_3$.

Illustrative multifunctional carboxylic acids include, but are not limited to, malonic acid, glutaric acid, citric acid, or a combination of any two or more thereof. Where the multifunctional carboxylic acid includes malonic acid, in some embodiments, the copper:malonic acid ration may be from about 2:1 to about 3.5:1. Where the multifunctional carboxylic acid includes glutaric acid, in some embodiments, the copper:glutaric acid ration is from about 5:1 to about 9:1.

In preparing the catalyst, the aqueous copper salt solution is applied to the metal oxide carrier until an incipient wetness impregnation ("IWI"; filling 90% of pore volume of the metal oxide carrier, as measured by $N_2$ adsorption), is reached. The temperature at which the impregnation phase of the catalyst preparation is conducted is held constant throughout the impregnation process. The temperature may be from about 20° C. to about 90° C.

After impregnation of the metal oxide carrier with the aqueous copper salt solution, the thus impregnated carrier is dried at a temperature from about 100° C. to about 125° C., until substantially all of the free water in the impregnated carrier is removed, and a dried, impregnated carrier is formed. In some embodiments, the temperature for drying is about 110° C.

The dried impregnated carrier is then heat-treated in air to form the catalyst. The heat-treating temperature may vary from about 250° C. to about 750° C. In some embodiments, the heat-treating temperature is from about 300° C. to about 400° C. The heat-treating may be conducted for as long as necessary. This may be from, in some embodiments, from about 5 minutes to about 5 hours.

The catalyst may contain from about 5 wt % to about 50 wt % cupric oxide (CuO). This may include from about 5 wt % to about 40 wt %, or from about 15 wt % to about 35 wt %, in other embodiments. As noted, bismuth may optionally be present in the aqueous copper salt solution, and accordingly bismuth may optionally be present in the catalyst. Where bismuth is present, it may be present as bismuth oxide in the catalyst up to about 5 wt %. This may include from about 0.5 wt % to about 5 wt %, or from about 2 wt % to about 4 wt %, in various embodiments.

The copper dispersion on said catalyst is at least about 0.5% as measured by the selective $N_2O$ dissociation method as described vide infra. In another embodiment, the copper dispersion includes from about 0.5% to about 15%.

As described above, the carrier may be a metal oxide. The metal oxide may variously be, a siliceous material, alumina, titania, zirconia, or a combination of any two or more thereof. The siliceous material may include silica or metal silicates, such as Group II and III metal silicates, including, but not limited to, clays which include aluminum silicates. The metal oxide carrier may also be comprised of gamma-alumina. In some embodiments, the carrier material is silica ($SiO_2$). The metal oxide carrier may have a pore volume from about 0.3 ml/g to about 2.5 ml/g. Where the metal oxide carrier is silica, the silica may also have a pore volume in some embodiments, from about 1 ml/g to about 1.8 ml/g. Where the metal oxide carrier is alumina, the alumina may also have a pore volume in some embodiments, from about 0.5 ml/g up to about 1.5 ml/g. Impurities in the metal oxide carrier may be present in small amounts. Other silicate materials with different compositions may be used. Silica-only carriers, without other metals, may also be used effectively.

Ethynylation processes generally vary from practitioner to practitioner. It is believed that the catalysts described above with reference to their preparation will be applicable to all specific types of ethynylation processes. For example, an ethynylation process using the catalyst of this invention can be that as described in U.S. Pat. No. 3,920,759.

It will be appreciated that the ethynylation catalysts described herein will require activation prior to use in any chemical synthesis processes, including ethynylation. As described in U.S. Pat. No. 3,920,759, a catalyst is activated by means of the introduction of acetylene into a formaldehyde-catalyst reaction medium. When activating the catalyst, the catalyst in situ is subjected to the simultaneous action of the reactants at the required pressure in a substantially aqueous medium at a temperature of about 60° C. to about 120° C. At temperatures substantially outside this range, or in strongly basic or acidic media, or acetylene partial pressures greater than 2 atmospheres, or in the substantial absence of either formaldehyde or acetylene, poor catalyst formation is generally observed. In some embodiments, the catalyst generation temperature is from about 60° C. to about 120° C. The pH of the aqueous medium is typically in the range of about 3 to about 10. In some embodiments, the pH of the aqueous medium is from about 5 to about 6, and preferably 5 to 6. The concentration of formaldehyde in the aqueous medium is ordinarily in the range of about 5 wt % to about 60 wt %. This may include from at least 10 wt % to about 60 wt %, or from about 30 wt % to about 40 wt %, in various embodiments.

The partial pressure of acetylene over the aqueous medium is from about 0.1 atmospheres (atm) to about 1.9 atm. In some embodiments, the partial pressure of acetylene over the aqueous medium may be from about 0.4 atm to about 1.5 atm.

In carrying out the catalyst activation, nitrogen or another substantially inert gas such as methane or carbon dioxide may be present, as may also other common components of crude acetylene, such as methyl acetylene and ethylene. Oxygen, if present at all, is substantially excluded from gas feeds during activation and ethynylation, for safety reasons. In small catalyst batches, the ethynylation catalyst may be slurried in cold neutral formaldehyde solution and the acetylene introduced as the slurry is heated. Equivalent results are obtained by heating the catalyst slurry with formaldehyde at a relatively low temperature, such as 70° C., for a period of several hours before introducing acetylene. For larger batches, the ethynylation catalyst may be introduced incrementally to a hot, neutral formaldehyde solution under acetylene pressure. The aqueous solution may advantageously be a stream containing propargyl alcohol and/or butynediol, e.g., a recycle stream.

The catalyst activation reaction is typically continued until the cupric copper is substantially completely converted to cuprous copper form, which, with the cupric precursors, generally requires 4 to 48 hours after all the precursor has been contacted under the prescribed conditions. Additionally, the prescribed conditions of temperature, pH and acetylene/formaldehyde concentration balance and range will be maintained throughout the catalyst activation. However, departures from the prescribed conditions during the course of the preparation reaction can be tolerated, as the reaction is relatively insensitive to minor changes in operating conditions.

The pH of the aqueous medium normally decreases as the reaction proceeds, at a rate and to an extent, which tends to increase with the initial acidity of the reaction medium and also with the reaction temperature. Accordingly, the pH may be controlled from 3 to 10, by operating at a temperature from about 60° C. to about 120° C. Additional control may be achieved by adding small amounts of an acid acceptor to the reaction. Illustrative acid acceptor may include, but are not limited to, sodium acetate. Further control may be achieved by carrying out the catalyst generation as a continuous stirred reaction, fresh neutral formaldehyde solution being continuously introduced into an agitated reaction zone, (any acidic effluent may, if desired, be filtered away from the copper-containing particles) as the reaction proceeds, all the while maintaining the acetylene partial pressure.

The ethynylation reaction comprises contacting an activated ethynylation catalyst at a partial pressure of not more than about 1.9 atm with an aqueous slurry of the catalyst as above described, in a continuous stirred reaction at a temperature from about 80° C. to about 120° C. The formaldehyde and acetylene may be continuously fed into the reaction zone where they are introduced into and below the surface of, the aqueous catalyst slurry, and thoroughly mixed into the same by vigorous agitation, and effluent is continuously withdrawn.

The reaction temperature for ethynylation is typically from about 60° C. to about 120° C., This may include a reaction temperature of about 80° C. to about 115° C., or from about 85° C. to about 110° C. Advantageously, the pH of the reaction mixture is from about 3 to about 10. This may include a pH of about 4.5 to about 7. The pH may be maintained by ion exchange or acid acceptor treatment of the continuous feed or by addition of a suitable buffering agent.

The formaldehyde concentration in the liquid medium in contact with the slurried catalyst in the course of the ethynylation reaction may be from about 0.5 wt % to about 60 wt % under stead state conditions. This may include a concentration from about 0.5 wt % to about 37 wt %. The acetylene partial pressure may be at least 0.5 atm. Advantageously, the acetylene partial pressure may be from about 0.4 atm to about 1.9 atm. In some embodiments, the acetylene partial pressure above the aqueous medium may be from about 0.5 atm to about 1.5 atm, and the catalyst will be present from about 1 wt % to 20 wt %. The acetylene partial pressure may be determined as the total pressure minus the absolute pressure of water and formaldehyde at the reaction temperature. As in the catalyst generation, crude acetylene may be used, but for safety reasons it should be advantageously substantially free of oxygen.

The effluent from the reaction zone may be heated and/or subjected to reduced pressure to volatilize formaldehyde, propargyl alcohol and a portion of the water which are condensed and combined with supplemental concentrated formaldehyde for recycling to the ethynylation reactor, purging buildup of methanol at convenient intervals in a continuous operation, and sending the balance of effluent as aqueous alkynol directly to hydrogenation. Alternatively, effluent from the reaction zone may be fed to a conventional plug flow ethynylation to react any excess formaldehyde.

In another aspect, a catalyst useful in hydrogenations is provided. For example, the catalyst may be used in the hydrogenation of butyraldehyde to n-butanol. The catalyst may be prepared by an impregnation process similar to that as described above. The impregnation technique includes the addition of a multifunctional carboxylic acid to an impregnation solution whereby the dispersion of the active metal is dramatically improved. The catalyst is a copper oxide-based catalyst that is highly active in the hydrogenation of butyraldehyde to n-butanol.

In the impregnation process, the multifunctional carboxylic acid is added to an aqueous solution of copper ions to prepare a dispersion that is then applied to a metal oxide carrier to form an impregnated metal oxide carrier. The impregnated metal oxide carrier is then dried to remove free water, followed by heat-treating to prepare the catalyst.

The copper ions may be the result of the aqueous dissolution of a copper salt in water. Illustrative copper salts are described above, and include, but are not limited to, copper sulfate and copper nitrate. In some embodiments, the copper salt is $Cu(NO_3)_2$.

Illustrative multifunctional carboxylic acids are also described above, and include, but are not limited to glutaric acid, citric acid, and malonic acid. In some embodiments, of the hydrogenation catalyst, glutaric acid is employed. When preparing the aqueous solution, the multifunctional carboxylic acid may be added to a nearly saturated solution of copper. For example, where the copper is present from the dissolution of copper nitrate, the saturated solution at room temperature is approximately 16 wt % in the water. A ratio of copper ions to acid on a mol basis is from approximately 4 to 8. In some embodiments the ratio of copper ions to acid on a mol basis is approximately 6. In some embodiments, ratio of copper ions to glutaric acid on a mol basis is from approximately 4 to 8. In some embodiments, ratio of copper ions to glutaric acid on a mol basis is approximately 6. It has been shown that the activity of the catalyst increases proportionally to the copper surface area on the support. See Example 1.

In another aspect, a method is provided for preparing a hydrogenation catalyst using pyrolysis conditions in comparison to the calcination conditions described above. The difference being that under pyrolysis conditions, the heat-treatment of the dried impregnated carrier is conducted in an oxygen-limited atmosphere as compared to being done in air in the calcination process. As used herein, the term "oxygen-limited atmosphere" refers to the heat treatment being done in an atmosphere containing less than about 21 vol % of $O_2$. In some embodiments, this includes where the atmosphere contains less than about 5 vol % of $O_2$. In some embodiments, this includes where the atmosphere is substantially oxygen-free (i.e. $O_2$-free). A substantially oxygen-free atmosphere is one in which steps are taken to remove and not introduce oxygen to the atmosphere and it may be conducted under an inert gas such as nitrogen, hydrogen, helium, neon, or argon.

It has been found that by performing the heat-treatment under pyrolysis (i.e. oxygen-limited) conditions, the Cu dispersion is substantially improved on the metal oxide carrier, and lower amounts of the multifunctional carboxylic acid are requires. Without being bound by theory, it is believed that the pyrolysis conditions lower the severity of exotherm experienced during calcination, the exotherm being responsible for sintering of the copper species. It was also observed that performance and Cu dispersion go through a maximum, and then decrease rapidly with increasing carboxylic acid addition. It was observed that this decrease in performance at higher acid addition amounts is due to the increased exotherm that occurs upon calcination and decomposition (combustion) of the carboxylic acid.

The present invention, thus generally described, will be understood more readily by reference to the following examples, which are provided by way of illustration and are not intended to be limiting of the present invention.

The present technology thus described, it will be more specifically described and explained by means of the following examples, which are not to be considered as limiting but merely illustrative of the invention. All parts and proportions therein as well as in the appended claims are by weight unless otherwise specified.

EXAMPLES

Ethynylation Catalysis

Testing was carried out in two steps. First, the catalyst was activated to form the active copper acetylide. Second, the activated catalyst was then transferred to the reaction vessel.

Catalyst Activation.

Catalyst activation was carried out in a 4-port quartz reactor flask containing 100 ml formalin (37 wt % formaldehyde in water). The pH of the formalin was initially adjusted to about 8 by adding 1.5 M NaOH. Next, 15 g of catalyst were added to the pH adjusted formalin. The flask was purged with nitrogen, stirring was started, and acetylene was introduced at 50 m/min to the catalyst-formalin slurry at room temperature. The flask was then lowered into a recirculating water bath and heated to 80° C. This procedure forms the active Cu(I) acetylide species [$Cu_2C_2$].

The formic acid produced in this step was continuously neutralized by adding 1.5 M NaOH to the slurry, thus keeping the pH at about 8. After 5 hours, the reactor was cooled to room temperature under flowing acetylene. Once it reached room temperature, acetylene was purged from the flask with nitrogen, the reactor was disassembled, and the slurry removed. It was weighed, centrifuged, and decanted, leaving wet catalyst ready for activity testing.

Ethynylation Reaction.

Reaction studies were carried out using 0.5 g of the activated catalyst (dry basis) loaded into a stainless steel stirred autoclave containing 45 ml formalin. As with the activation procedure, the pH of the formalin was initially adjusted to about 8. The reactor was purged with nitrogen and acetylene before starting the reaction. The reactor was operated in a semi-batch fashion while stirring at 1450 RPM. At the start, acetylene from pressurized ballast cylinders was introduced to the reactor through a pressure regulator set at 15 psig (the reaction pressure), and the reactor was heated at approximately 2° per min to 80° C. After 5 hours, the reactor was cooled in flowing acetylene and subsequently purged with nitrogen. The slurry was removed, centrifuged, and decanted. The product mixture was analyzed by gas chromatography in which butynediol (primary product) and propargyl alcohol (product intermediate) were quantified. Because formaldehyde is not readily detected by gas chromatographic analysis, a sodium sulfite titration method was used to determine the amount of formaldehyde remaining in the product. Thus, overall formaldehyde conversion was calculated based on 300 min reaction time and 0.5 g catalyst; and the initial catalytic reaction rate in terms of kg formaldehyde converted per kg of catalyst per hour was calculated.

Activity Comparison.

Conditions are given in the "catalyst testing procedure" section. The process/catalyst activity is measured by the rate of formation of butynediol as measured as the moles of butynediol produced per minute per gram of catalyst [mol/min/g-cat].

Copper Dispersion.

The dispersion of Cu is calculated by dividing the moles of surface Cu(0) atoms to the moles of total Cu(0) atoms on the catalyst. It is measured by a selective $N_2O$ dissociation method that is standard practice in the art (Chinchen et al. *Journal of Catalysis* 103(1): 79-86. (1987)). The procedure for determining Cu dispersion and Cu surface area is as follows: The calcined catalyst is reduced at 210° C. for 90 minutes after a 5° C./min ramp in 5% $H_2$/95% $N_2$ gas. The reduced catalyst is cooled to 60° C. and held at that temperature for 15 minutes while it is purged with He. At 60° C., 2% $N_2O$/98% He is passed over the reduced catalyst and the evolution of $N_2$ is observed by a thermal conductivity detector in conjunction with a liquid Ar cooled trap which condenses unreacted $N_2O$. The measurement is completed when no further $N_2$ is evolved. The amount of $N_2O$ consumed and $N_2$ evolved to follow the reaction chemistry:

$$N_2O + 2Cu \rightarrow N_2 + Cu_2O,$$

on the surface of the reduced catalyst and the reaction does not occur in the bulk (i.e. subsurface) Cu(0) layers. The Cu dispersion is then calculated by taking the ratio of surface Cu(0) atoms per gram catalyst measured by this method (i.e. atoms $N_2$ evolved multiplied by 2) divided by the total number of Cu(0) atoms per gram catalyst.

Catalyst Activation.

In an inert atmosphere (nitrogen), heat the catalyst up in the reactor to 170 C and dwell until the temperature is stable. Introduce 5 vol % of hydrogen gas and decrease the inert gas by 5 vol % to maintain a constant gas volumetric flowrate and dwell for 1 hour. Increase the hydrogen concentration to 10 vol % and decrease the nitrogen another 5 vol % to maintain a constant gas volumetric flowrate and dwell for 1 hour. Increase the hydrogen concentration to 20 vol % and decrease the nitrogen another 10 vol % to maintain a constant gas volumetric flowrate and dwell for 1 hour. Increase the hydrogen concentration to 50 vol % and decrease the nitrogen another 30 vol % to maintain a constant gas volumetric flowrate and dwell for 1 hour. Increase the hydrogen concentration to 100 vol % such that the total volumetric flow rate decreases to 80% of the original flow rate and dwell for 1 hour. Once this procedure is completed, the catalyst has been reduce whereby CuO has been converted to Cu(0) and the catalyst is ready to be set to reaction conditions.

Reaction Conditions.

The butyraldehyde hydrogenation can be run as a vapor phase reaction or as a high-pressure trickle bed reaction. The gas phase reaction conditions are: 100° C., 2.1 barg, LHSV 3 hr$^{-1}$, and a ratio of H$_2$:butyraldehyde of 30:1. The reaction data provided in entries 1-3 are under these conditions. The reaction was monitored by a gas chromatograph with a flame ionization detector calibrated for the involved compounds. The catalysts prepared show nearly 100% selectivity.

Characterization of the Catalyst.

In order to note the coverage of Cu and Bi oxides around the support, Scanning Electron Microscopy (SEM) was used as seen in FIGS. 1-42. The brighter portions of the catalyst shows the copper and bismuth oxides, whereas the darker gray portions indicate the support oxide.

Example 1

A series of four catalyst are synthesized by applying a solution containing metal nitrates (14.0 wt % Cu, 2.6 wt % Bi) and 0-10 wt % citric acid (CA) to a silica support until reaching incipient wetness impregnation (filling 90% of the pore volume (measured by N$_2$ adsorption) of the support) while mixing the powder. The pore volume of the silica is 1.4 ml/g. The powder is then dried at 110° C. for at least 12 hours. The dried powder is then calcined in air at 500° C. for 2 hours following a 1° C./min ramp to the final temperature.

Figure 43:
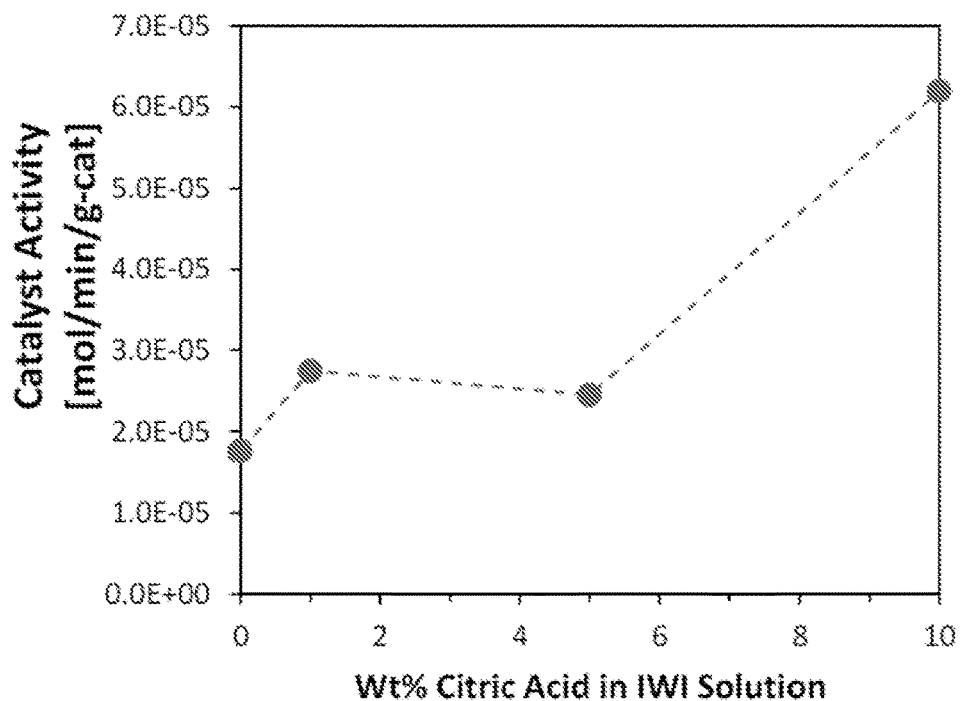
FIG. 43 is a graph illustrating the improved activity of the catalyst from Samples 1A-C, observed in the ethynylation reaction.

Samples Example-1A (0 wt % CA), (1 wt % CA), Example-1B (5 wt % CA), and Example-1C (10 wt % CA). The catalysts had the nominal composition of 21.3 wt % CuO, 3.7 wt % Bi$_2$O$_3$, and 75 wt % SiO$_2$. FIG. 43 is a graph illustrating the improved activity of the catalyst observed in the ethynylation reaction (combination of 2 moles of formaldehyde with 1 mole of acetylene to form one mole of 1,4-butynediol) by adding increasing amounts of citric acid to the impregnation (IWI) solution. The improvement to Cu dispersion can be observed qualitatively in the backscatter SEM images with increasing citric acid content in the impregnation solution FIGS. 1-6.

Example 2

A series of five catalyst are synthesized by applying a solution containing metal nitrates (14.0 wt % Cu, 2.6 wt % Bi) and 0-10 wt % glutaric acid (GA) to a silica support until reaching incipient wetness impregnation (filling 90% of the pore volume (measured by N$_2$ adsorption) of the support) while mixing the powder. The pore volume of the silica is 1.4 ml/g. The powder is then dried at 110° C. for at least 12 hours. The dried powder is then calcined in air at 500° C. for 2 hours following a 1° C./min ramp to the final temperature.

Figure 44:
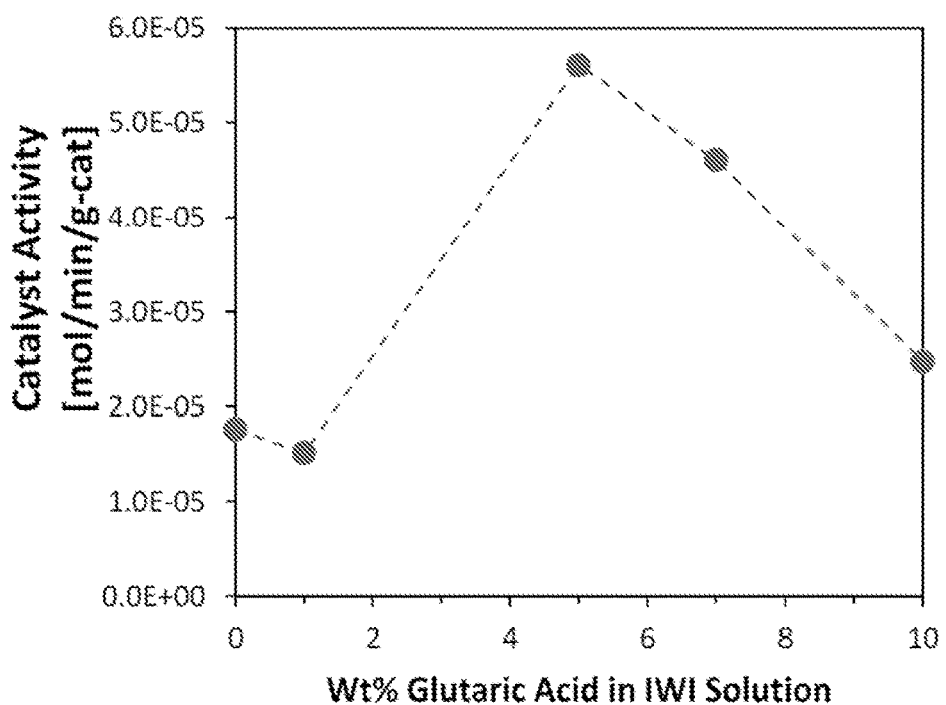
FIG. 44 is a graph illustrating the improved activity of the catalyst from Samples 2A-E, observed in the ethynylation reaction.

Samples Example 2A (0 wt % GA), Example 2B (1 wt % GA), Example 2C (5 wt % GA), Example 2D (7 wt % GA), and Example 2E (10 wt % GA). The catalysts had the nominal composition of 21.3 wt % CuO, 3.7 wt % Bi$_2$O$_3$, and 75 wt % SiO$_2$. FIG. 44 illustrates the improved activity of the catalyst observed in the ethynylation reaction (combination of 2 moles of formaldehyde with 1 mole of acetylene to form one mole of 1,4-butynediol) by adding increasing amounts of glutaric acid to the impregnation solution. An interesting feature of the plot is the existence of a clear optimum in activity. The improvement to Cu dispersion can be observed qualitatively in the backscatter SEM images with increasing glutaric acid content in the impregnation solution. (FIGS. 7-16)

Example 3

A series of five catalyst are synthesized by applying a solution containing metal nitrates (15.3 wt % Cu, 1.0 wt % Bi) and 0-7.5 wt % malonic acid (MA) to a silica support until reaching incipient wetness impregnation (filling 90% of the pore volume (measured by N2 adsorption) of the support) while mixing the powder. The pore volume of the silica is 1.4 mL/g. The powder is then dried at 110° C. for at least 12 hours. The dried powder is then calcined in air at 500° C. for 2 hours following a 1° C./min ramp to the final temperature.

Figure 45:
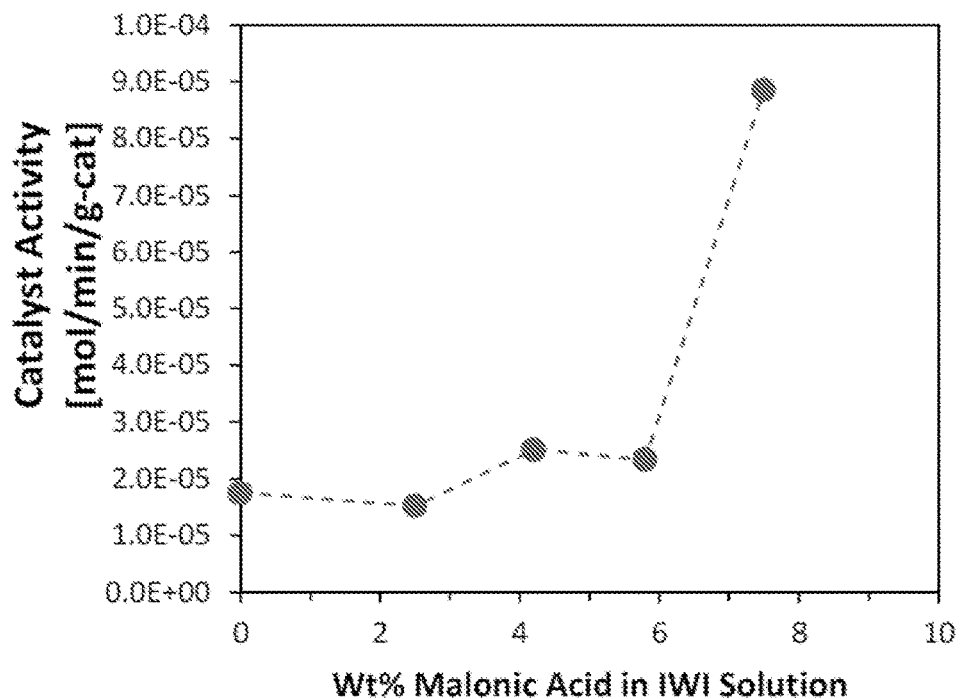
FIG. 45 is a graph illustrating the improved activity of the catalyst from Samples 3A-E, observed in the ethynylation reaction.
Figure 46:
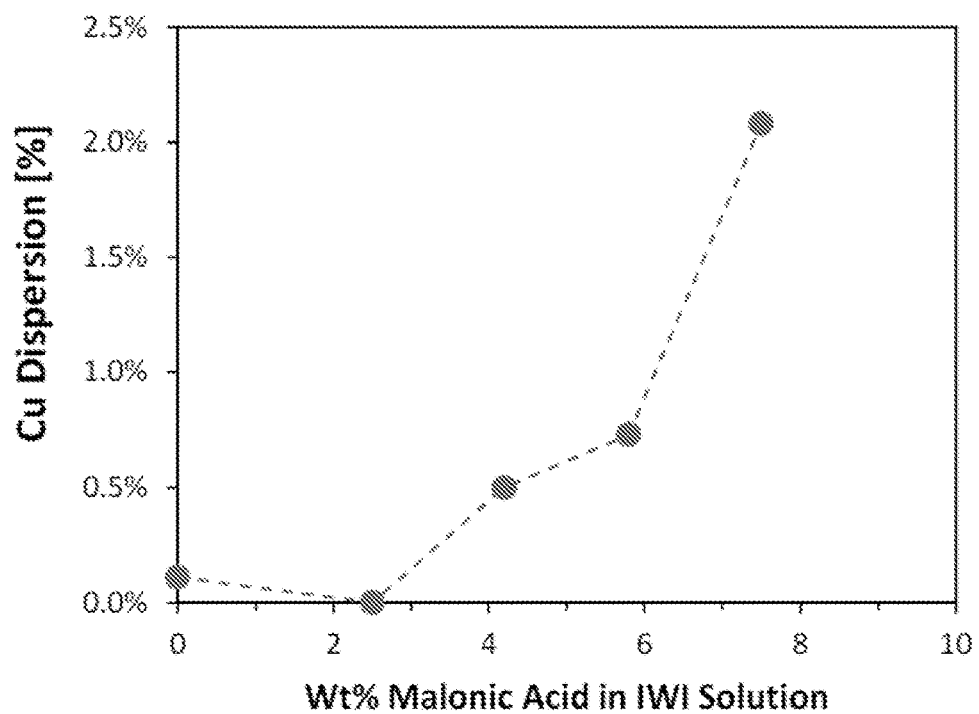
FIG. 46 is a graph illustrating the improvement to Cu dispersion in Example 3.

Samples Example 3A (0 wt % MA), Example 3B (2.5 wt % MA), Example 3C (4.2 wt % MA), Example 3D (5.8 wt % MA), and Example 3E (7.5 wt % MA). The catalysts had the nominal composition of 29.2 wt % CuO, 1.7 wt % Bi$_2$O$_3$, and 69.1 wt % SiO$_2$. FIG. 45 illustrates the improved activity of the catalyst observed in the ethynylation reaction (combination of 2 moles of formaldehyde with 1 mole of acetylene to form one mole of 1,4-butynediol) by adding increasing amounts of malonic acid to the impregnation solution. The improvement to Cu dispersion can be observed quantitatively in FIG. 46 below and qualitatively in the backscatter SEM images with increasing malonic acid content in the impregnation solution (FIGS. 17-26).

Example 4

A series of four catalyst are synthesized by applying a solution containing metal nitrates (15.3 wt % Cu, 1.0 wt % Bi) and 0-7.5 wt % glutaric acid (GA) to a silica support until reaching incipient wetness impregnation (filling 90% of the pore volume (measured by N$_2$ adsorption) of the support) while mixing the powder. The pore volume of the silica is 1.7 ml/g. The powder is then dried at 110° C. for at least 12 hours. The dried powder is then calcined in air at 500° C. for 2 hours following a 1° C./min ramp to the final temperature.

Figure 47:
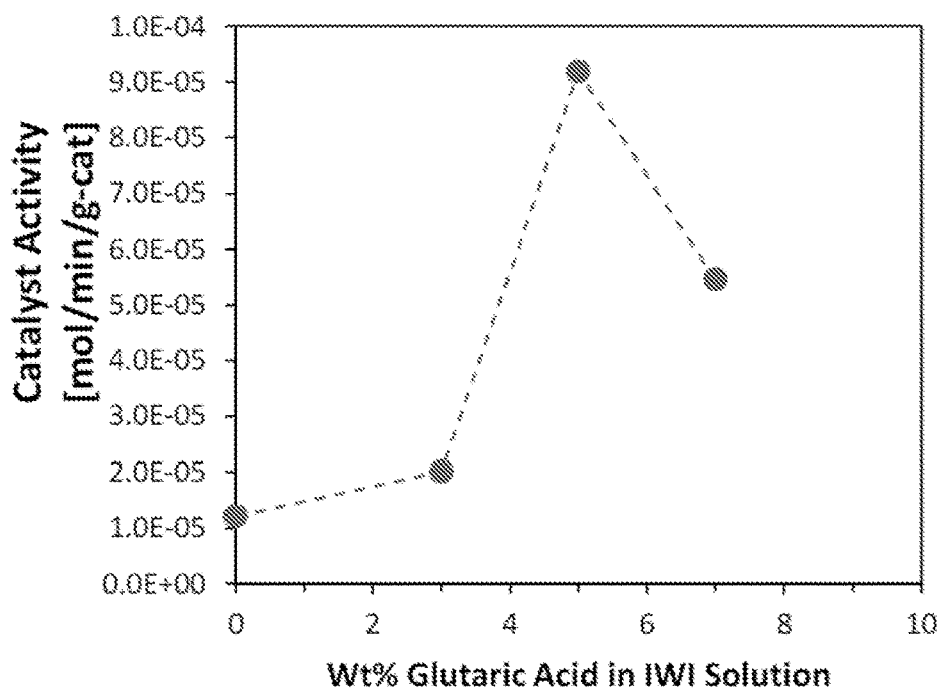
FIG. 47 is a graph illustrating the improved activity of the catalyst from Samples 4A-D, observed in the ethynylation reaction.
Figure 48:
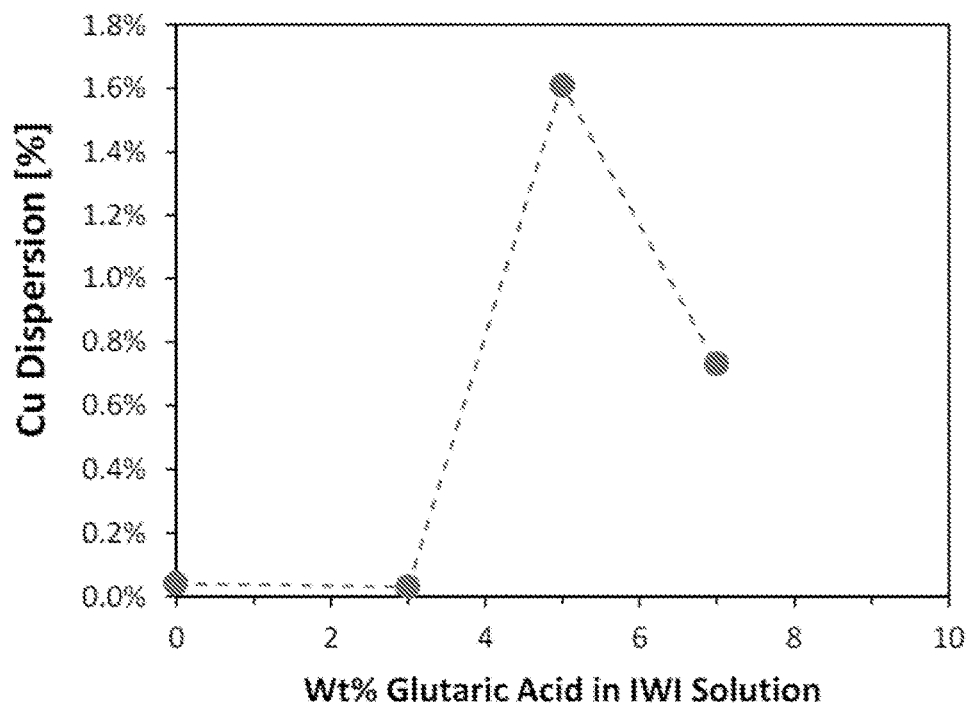
FIG. 48 is a graph illustrating the improvement to Cu dispersion in Example 4.

Samples Example 4A (0 wt % GA), Example 4B (3.0 wt % GA), Example 4C (5.0 wt % GA), and Example 4D (7.0 wt % GA). The catalysts had the nominal composition of 29.1 wt % CuO, 1.7 wt % Bi$_2$O$_3$, and 69.2 wt % SiO$_2$. FIG. 47 illustrates the improved activity of the catalyst observed in the ethynylation reaction (combination of 2 moles of formaldehyde with 1 mole of acetylene to form one mole of 1,4-butynediol) by adding increasing amounts of glutaric acid to the impregnation solution. The improvement to Cu dispersion can be observed quantitatively in FIG. 48, may also be observed in the backscatter SEM images with increasing glutaric acid content in the impregnation solution. There is a clear correlation between the Cu dispersion and the catalyst activity (FIGS. 27-32).

Example 5

A series of five catalyst are synthesized by applying a solution containing metal nitrates (7.7 wt % Cu, 0.5 wt % Bi)

and 1.5-7.0 wt % glutaric acid (GA) to a silica support until reaching incipient wetness impregnation (filling 90% of the pore volume (measured by $N_2$ adsorption) of the support) while mixing the powder. The pore volume of the silica is 1.7 ml/g. The powder is then dried at 110° C. for at least 12 hours. The dried powder is then calcined in air at 500° C. for 2 hours following a 2° C./min ramp to the final temperature.

Figure 49:
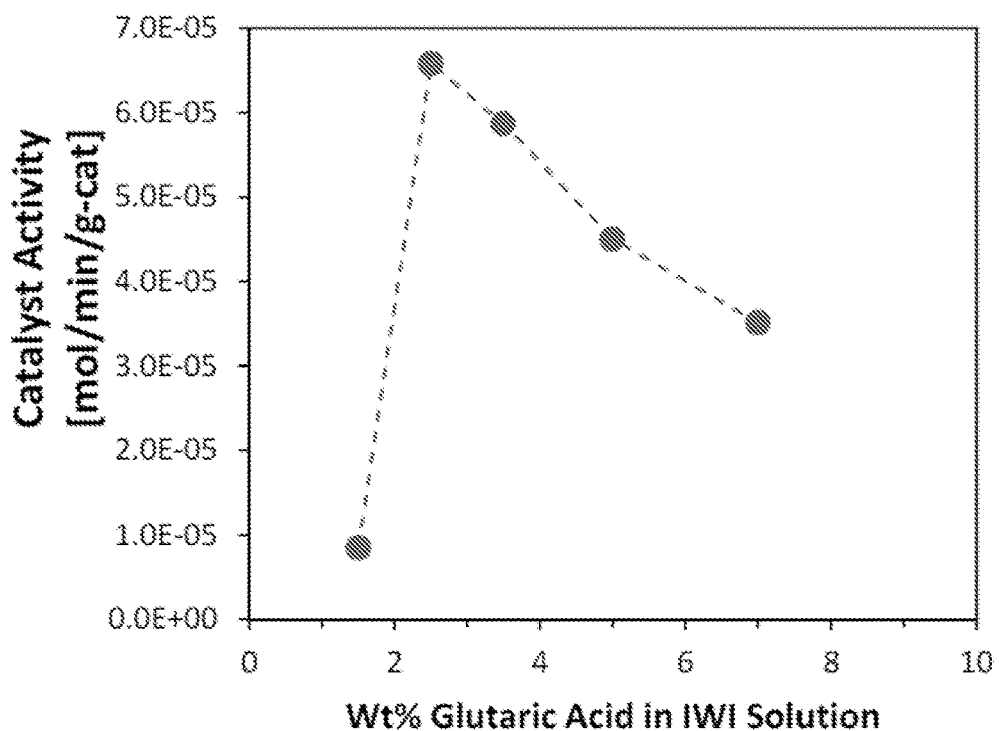
FIG. 49 is a graph illustrating the improved activity of the catalyst from Samples 5A-E, observed in the ethynylation reaction.

Samples Example 5A (1.5 wt % GA), Example 5B (2.5 wt % GA), Example 5C (3.5 wt % GA), Example 5D (5.0 wt % GA), Example 5E (7.0 wt % GA). The catalysts had the nominal composition of 15.1 wt % CuO, 0.9 wt % $Bi_2O_3$, and 84.0 wt % $SiO_2$. FIG. 49 illustrates the improved activity of the catalyst observed in the ethynylation reaction (combination of 2 moles of formaldehyde with 1 mole of acetylene to form one mole of 1,4-butynediol) by adding increasing amounts of glutaric acid to the impregnation solution. This plot shows that the metal:acid ratio, of about 6 is optimum for glutaric acid and Cu/Bi nitrates. The improvement to Cu dispersion can be observed qualitatively in the backscatter SEM images with increasing glutaric acid content in the impregnation solution. (FIGS. 33-42).

Example 6

A series of five catalyst are synthesized by applying a solution containing metal nitrates (15.3 wt % Cu, 1.0 wt % Bi) and 5.0 wt % glutaric acid to a silica support until reaching incipient wetness impregnation (filling 90% of the pore volume (measured by $N_2$ adsorption) of the support) while mixing the powder. The pore volume of the silica is 1.7 ml/g. The powder is then dried at 110° C. for at least 12 hours. The dried powder is then calcined in air at 250-500° C. for 2 hours following a 2° C./min ramp to the final temperature.

Figure 50:
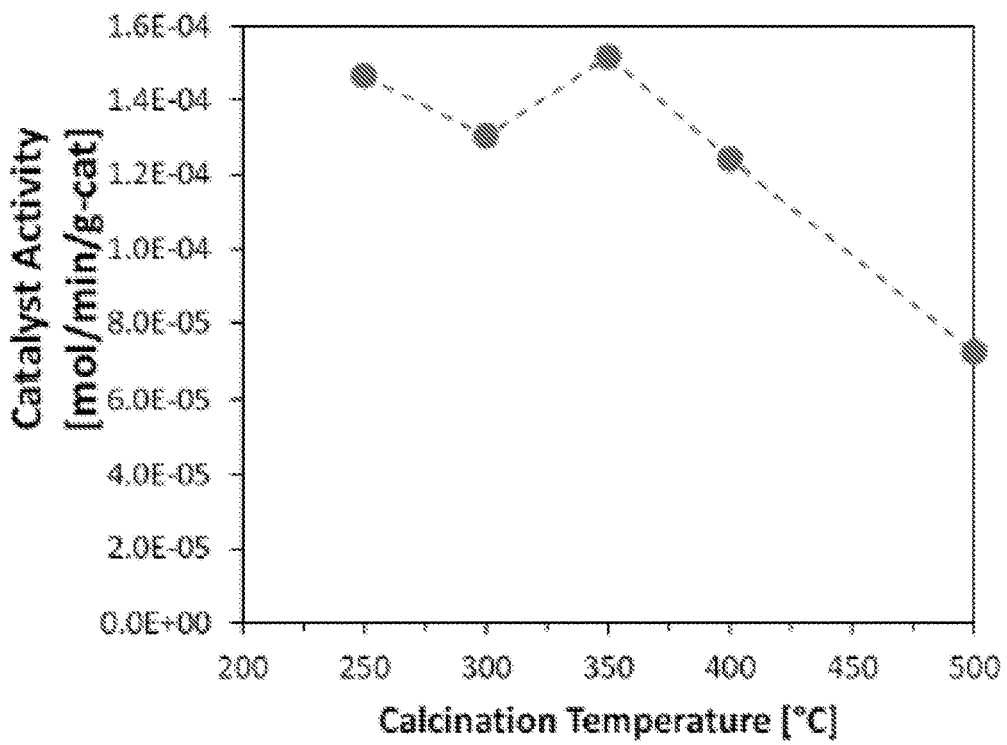
FIG. 50 is a graph illustrating the improved activity of the catalysts of Examples 6A-E.
Figure 51:
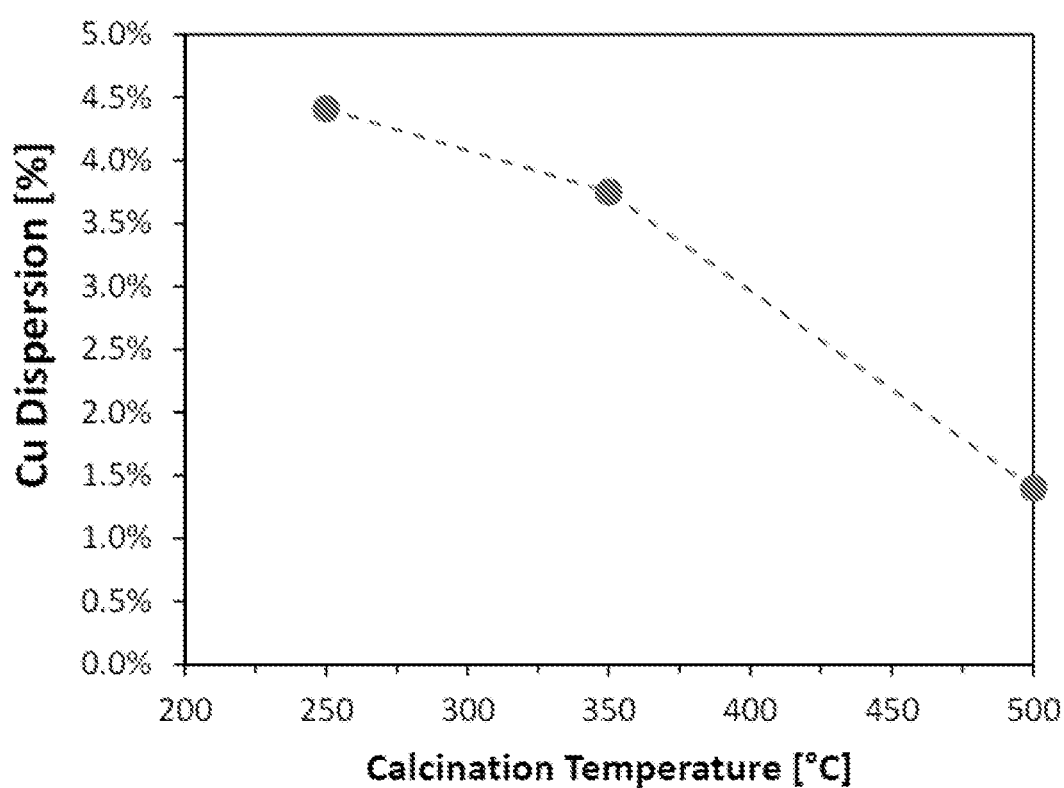
FIG. 51 is a graph illustrating the improvement to Cu dispersion for Samples 6A, 6C and 6E.

Samples Example 6A (250° C.), Example 6B (300° C.), Example 6C (350° C.), Example 6D (400° C.), and Example 6E (500° C.). The catalysts had the nominal composition of 33.4 wt % CuO, 1.9 wt % $Bi_2O_3$, and 64.7 wt % $SiO_2$. FIG. 50 illustrates the improved activity of the catalysts of Examples 6A-E observed in the ethynylation reaction (combination of 2 moles of formaldehyde with 1 mole of acetylene to form one mole of 1,4-butynediol) by varying the calcination temperature between 250-500° C.; 350° C. being the optimal value to fully decompose any metal salts or organic acid on the catalyst. The improvement to Cu dispersion for Examples 6A, 6C and 6E can be observed quantitatively in FIG. 51 which correlates with the activity of the catalyst.

Hydrogenation Catalysis

Methodology.

Cu dispersions are measured by a selective $N_2O$ dissociation method that is standard practice in the art (Chinchen, G. C., et al. *Journal of Catalysis* 103(1): 79-86 (1987). The procedure for determining Cu dispersion and Cu surface area is as follows. The calcined catalyst is reduced at 210° C. for 90 minutes after a 5° C./min ramp in 5% $H_2$/95% $N_2$ gas. The reduced catalyst is cooled to 60° C., and held at that temperature for 15 minutes while it is purged with He. At 60° C., 2% $N_2O$/98%, and He is passed over the reduced catalyst and the evolution of $N_2$ is observed by a thermal conductivity detector in conjunction with a liquid Ar cooled trap which condenses unreacted $N_2O$. The measurement is completed when no further $N_2$ is evolved. The amount of $N_2O$ consumed, and $N_2$ evolved, is assumed to follow the reaction chemistry $N_2O+2Cu \rightarrow N_2+Cu_2O$ on the surface of the reduced catalyst and the reaction does not occur in the bulk (i.e. subsurface) Cu layers. The Cu dispersion is then calculated by taking the ratio of surface Cu atoms per gram catalyst measured by this method (i.e. atoms $N_2$ evolved multiplied by 2) divided by the total number of Cu atoms per gram catalyst.

Example 7

Three catalysts were synthesized by applying a solution containing copper nitrate (16.0 wt % Cu) and 0 or 5 wt % glutaric acid (GA), to a silica support until reaching incipient wetness impregnation (filling 90% of the pore volume of the support, as measured by $N_2$ adsorption) while mixing the powder. The pore volume of the silica was 1.7 mL/g. The powder was then dried at 110° C. for at least 12 hours. The dried powder was then heated at a 1° C./min ramp to a final temperature of 350° C. or 500° C., where it was calcined in air for 2 hours.

Table 1 below gives the activity data for the hydrogenation of butyraldehyde to butanol, the copper dispersion of the said catalysts, the amount of glutaric acid used in modifying the incipient wetness impregnation (IWI) solution, the corresponding loading, and the calcination temperature. Entry 2 demonstrates the improvement to activity and dispersion over Entry 1, when modifying the IWI solution with glutaric acid. Entry 3 demonstrates that calcination optimization could further enhance activity and copper dispersion. It has been found that the catalyst activity appears to be directly proportional to the copper surface area of the catalyst. For example, increasing the Cu(0) can increase the activity of the catalyst to a similar degree.

TABLE 1

| Entry | GA (wt %) | Cu (wt %) | Calc. Temp. (° C.) | Activity[a] | Cu(0) Disp. (mol %) | Cu(0) Surface Area[b] |
|---|---|---|---|---|---|---|
| 1 | 0.0 | 20.0 | 500 | 0.05 | 0.01 | 0.01 |
| 2 | 5.0 | 30.4 | 500 | 5.28 | 1.07 | 2.29 |
| 3 | 5.0 | 26.6 | 350 | 16.14 | 2.97 | 5.49 |

[a]Units are mol butyraldehyde reacted/kg-cat/hour
[b]Units are $m^2Cu(0)$/g catalyst.

Example 8

It was demonstrated that acids other than glutaric, such as citric acid, can likewise improve the copper dispersion by modifying the IWI solution used in the synthesis. Four catalysts were synthesized by applying a solution containing copper nitrate (16.0 wt % Cu) and 0, 3, 5, or 7 wt % citric acid (CA) to a silica support until reaching incipient wetness impregnation (filling 90% of the pore volume of the support, as measured by $N_2$ adsorption) while mixing the powder. The pore volume of the silica was 1.7 mL/g. The powder was then dried at 110° C. for at least 12 hours. The dried powder was then heated at a 1° C./min ramp to a final temperature of 500° C., where the dried powder was calcined in air at 500° C. for 2 hours. Table 2 illustrates the improvement to Cu dispersion with the addition of citric acid into the impregnation solution.

TABLE 2

| Entry | CA (wt %) | Cu (wt %) | Calc. Temp. | Cu(0) Disp. (mol %) | Cu(0) Surface Area[b] |
|---|---|---|---|---|---|
| 1 | 0.0 | 20.0 | 500 | 0.01 | 0.01 |
| 4 | 3.0 | 18.4 | 500 | 0.02 | 0.03 |

TABLE 2-continued

| Entry | CA (wt %) | Cu (wt %) | Calc. Temp. | Cu(0) Disp. (mol %) | Cu(0) Surface Area[b] |
|---|---|---|---|---|---|
| 5 | 5.0 | 20.2 | 500 | 0.15 | 0.20 |
| 6 | 7.0 | 25.8 | 500 | 2.12 | 3.53 |

Example 9

The following examples demonstrate how different shapes and dimensions of silica supports still exhibit a significant improvement to Cu dispersion by adding glutaric acid (GA) at 5 wt % (Cu:GA~6). The catalysts were synthesized by applying a solution containing copper nitrate (16.0 wt % Cu) and 0-7 wt % glutaric acid to a silica support until reaching incipient wetness impregnation (filling 90% of the pore volume of the support, as measured by $N_2$ adsorption) while mixing the material. Different support shapes were utilized including powders, spheres, and extrudates. The pore volume of the powder was 1.7 mL/g, sphere 0.9 mL/g, and extrudate 0.7 mL/g. The resultant materials were then dried at 110° C. for at least 12 hours. The dried powder was then calcined in air at 500° C. for 2 hours, following a 1° C./min ramp to the final temperature. The dried spheres and extrudates were then calcined in air at 350° C. for 3 hours, following a/min ramp to the final temperature. Table 3 illustrates that the organic assisted impregnation is effective with support powders or shaped supports.

TABLE 3

| Entry | GA (wt %) | Cu (wt %) | Calc. Temp. (° C.) | Cu(0) Disp. (mol %) | Cu(0) Surf. Area[b] | Shape | Avg. Size |
|---|---|---|---|---|---|---|---|
| 1 | 0.0 | 20.0 | 500 | 0.01 | 0.01 | Powder | 45 μm |
| 2 | 5.0 | 30.4 | 500 | 1.07 | 2.29 | Powder | 45 μm |
| 7 | 0.0 | 12.9 | 350 | 4.36 | 3.62 | Sphere | 4 mm |
| 8 | 1.0 | 13.7 | 350 | 2.50 | 2.20 | Sphere | 4 mm |
| 9 | 2.0 | 14.5 | 350 | 2.14 | 2.00 | Sphere | 4 mm |
| 10 | 3.0 | 15.0 | 350 | 2.34 | 2.27 | Sphere | 4 mm |
| 11 | 4.0 | 17.1 | 350 | 6.18 | 6.81 | Sphere | 4 mm |
| 12 | 5.0 | 17.4 | 350 | 9.36 | 10.50 | Sphere | 4 mm |
| 13 | 6.0 | 16.5 | 350 | 5.26 | 5.59 | Sphere | 4 mm |
| 14 | 0.0 | 11.1 | 350 | 0.50 | 0.33 | Extrudate | 2 mm |
| 15 | 3.0 | 13.9 | 350 | 4.10 | 3.67 | Extrudate | 2 mm |
| 16 | 5.0 | 14.8 | 350 | 4.90 | 4.62 | Extrudate | 2 mm |
| 17 | 7.0 | 14.5 | 350 | 3.80 | 3.52 | Extrudate | 2 mm |

Example 10

The following entries demonstrated that a significant improvement to Cu dispersion could be achieved irrespective of catalyst support. Several catalysts were synthesized by applying a solution containing copper nitrate (16.0 wt % Cu) and 0-7 wt % glutaric acid to a gamma alumina until reaching incipient wetness impregnation (filling 90% of the pore volume of the support, as measured by $N_2$ adsorption) while mixing the material. The pore volume of the alumina powder was 0.6 mL/g. The resultant material was then dried at 110° C. for at least 12 hours. The dried powder was then calcined in air at 500° C. for 2 hours, following a 1° C./min ramp to the final temperature. Table 4 illustrates the copper dispersion as a function of amount of glutaric acid on alumina.

TABLE 4

| Entry | GA (wt %) | Cu (wt %) | Calc. Temp. | Cu(0) Disp. (mol %) | Cu(0) Surface Area[b] |
|---|---|---|---|---|---|
| 18 | 0.0 | 8.0 | 500 | 1.38 | 0.71 |
| 19 | 3.0 | 9.8 | 500 | 3.88 | 2.45 |
| 20 | 5.0 | 9.6 | 500 | 5.75 | 3.56 |
| 21 | 7.0 | 9.2 | 500 | 5.91 | 3.50 |

Example 11

This example demonstrates that changing the calcination atmosphere from air to nitrogen results in a substantial increase of Cu dispersion. These catalysts were synthesized by applying a solution containing copper nitrate (16.0 wt % Cu) and 0-5 wt % glutaric acid to a silica sphere support (4 mm) until reaching incipient wetness impregnation (filling 90% of the pore volume of the support, as measured by $N_2$ adsorption) while mixing the material. The pore volume of the silica was 0.9 mL/g. The material was then dried at 110° C. for at least 12 hours. The dried powder was then calcined in the specified atmosphere at 350° C. for 3 hours following a/min ramp to the final temperature. Table 5 illustrates the effects of pyrolysis v. air calcination on copper dispersion as a function of glutaric acid amount.

TABLE 5

| Entry | GA (wt %) | Cu (wt %) | Atmosphere | Cu(0) Disp. (mol %) | Cu(0) Surface Area[b] |
|---|---|---|---|---|---|
| 22 | 0.0 | 12.1 | Air | 1.12 | 0.87 |
| 23 | 3.0 | 14.8 | Air | 2.77 | 2.64 |
| 24 | 4.0 | 14.5 | Air | 4.63 | 4.32 |
| 25 | 5.0 | 14.5 | Air | 7.44 | 6.95 |
| 26 | 0.0 | 12.8 | Nitrogen | 2.66 | 2.19 |
| 27 | 3.0 | 15.5 | Nitrogen | 7.24 | 7.23 |
| 28 | 3.5 | 15.6 | Nitrogen | 9.95 | 10.00 |
| 29 | 4.0 | 15.4 | Nitrogen | 9.23 | 9.16 |

Example 12

Copper dispersions are prepared by pyrolyzing in a nitrogen atmosphere by which the decomposition (i.e. combustion) of the glutaric acid becomes less exothermic in nature. This occurs because $NO_2$ as an oxidizing agent as observed by more NO formation during the calcination in nitrogen than in the calcination with air. The following data illustrates that a weaker exotherm is exhibited by the sample when calcined in nitrogen, when compared to air. The lesser exotherm causes the catalyst to experience a lower overall temperature and undergo less sintering during calcination which in turn leads to higher Cu(0) surface area and catalyst activity. Table 6 illustrates the effects of pyrolysis v. air calcination on the exothermicity of the calcination process.

TABLE 6

| Entry | GA (wt %) | Atmosphere | Heat Released |
|---|---|---|---|
| 30 | 3.5 | Air | −163.9 J/g |
| 31 | 3.5 | Nitrogen | −126.8 J/g |
| 32 | 5.0 | Air | −232.8 J/g |
| 33 | 5.0 | Nitrogen | −159.0 J/g |

Thermal gravimetric analysis (TGA), differential scanning calorimetry (DSC), and mass spectrometer (MS) were carried out according to the following methodology. About 85 mg of sample was under 100 mL/min of the selected atmosphere gas. The sample was ramped from room temperature to 120° C. at 5° C./min, and held at that temperature for 10 minutes. The sample was then ramped to 400° C. at 5° C./min. The change in sample weight was monitored by thermal gravimetric analysis and the heat evolution by differential scanning calorimetry.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. A process for forming a catalyst for hydrogenation, dehydrogenation, hydrogenolysis, or ethynylation, the process comprising:
    impregnating a metal oxide carrier with an aqueous solution to form an impregnated carrier;
    drying the impregnated carrier to form a dried, impregnated carrier; and
    heat-treating the dried, impregnated carrier to form the catalyst;
    wherein:
       the aqueous solution comprises:
          a copper salt; and
          from about 1 wt % to about 15 wt % of a $C_3$-$C_6$ multifunctional carboxylic acid; and
       the catalyst consists of about 5 wt % to about 50 wt % copper oxide and optionally a bismuth salt.

2. The process of claim 1, wherein the copper salt comprises copper nitrate, copper sulfate, copper acetate, copper chloride, or copper citrate.

3. The process of claim 1, wherein the catalyst is an ethynylation catalyst and the aqueous solution further comprises the bismuth salt and the catalyst comprises up to about 5 wt % $Bi_2O_3$.

4. The process of claim 3, wherein the bismuth salt comprises bismuth nitrate, bismuth sulfate, bismuth acetate, bismuth chloride, or bismuth citrate.

5. The process of claim 1, wherein the multifunctional carboxylic acid is a $C_3$-$C_5$ multi-carboxylic acid.

6. The process of claim 1, wherein the catalyst is a hydrogenation, dehydrogenation, or hydrogenolysis catalyst and the aqueous solution consists essentially of the copper salt, from about 1 wt % to about 15 wt % of a $C_3$-$C_6$ multifunctional carboxylic acid, and, optionally, a precipitation agent.

7. The process of claim 1, wherein the aqueous solution comprises from about 2.5 wt % to about 7 wt % of the $C_3$-$C_6$ multifunctional carboxylic acid.

8. The process of claim 1, wherein the drying is carried out at a temperature from about 100° C. to about 125° C. for a period of time sufficient to remove substantially all free water present in the impregnated carrier, and the impregnating is carried out at a temperature of about 10° C. to about 90° C.

9. The process of claim 1, wherein the heat-treating comprises calcining in air.

10. The process of claim 1, wherein the heat-treating comprises pyrolyzing in an atmosphere substantially free of oxygen at a temperature from about 250° C. to about 750° C.

11. The process of claim 10, wherein the heat-treating comprises calcination in an oxygen-limited atmosphere has less than 21 vol % oxygen.

12. The process of claim 1, wherein the metal oxide carrier is a siliceous oxide comprising silica or silica and gamma-alumina.

13. The process of claim 1, wherein the ethynylation catalyst comprises from about 5 wt % to about 50 wt % CuO.

14. The process of claim 1, wherein a pore volume the metal oxide carrier is from about 0.3 ml/g to about 2.5 ml/g.

15. The process of claim 1, wherein a molar ratio of copper:multifunctional carboxylic acid is from about 1 to 15 when calcined in air.

16. The process of claim 1, wherein the catalyst is a hydrogenation catalyst and the process further comprises activating the hydrogenation catalyst by forming Cu(0) metal.

17. The process of claim 1, wherein the catalyst is an ethynylation catalyst and the process further comprises activating the ethynylation catalyst by forming Cu(I)acetylide.

18. A process for forming a catalyst for ethynylation, the process comprising:
impregnating a metal oxide carrier with an aqueous solution to form an impregnated carrier;
drying the impregnated carrier to form a dried, impregnated carrier;
heat-treating the dried, impregnated carrier to form the catalyst; and
activating the ethynylation catalyst by forming Cu(I) acetylide;
wherein:
the aqueous solution comprises:
a copper salt; and
from about 1 wt% to about 15 wt% of a $C_3$-$C_6$ multifunctional carboxylic acid; and
the catalyst comprises from about 5 wt% to about 50 wt% copper oxide.

19. The process of claim 1, wherein the copper salt comprises copper nitrate, copper sulfate, copper acetate, copper chloride, or copper citrate.

20. The process of claim 1, wherein the catalyst is an ethynylation catalyst and the aqueous solution further comprises a bismuth salt and the catalyst comprises up to about 5 wt% $Bi_2O_3$.

* * * * *

UNITED STATES PATENT AND TRADEMARK OFFICE
CERTIFICATE OF CORRECTION

PATENT NO. : 10,399,062 B2
APPLICATION NO. : 15/557578
DATED : September 3, 2019
INVENTOR(S) : Deutsch et al.

Page 1 of 1

It is certified that error appears in the above-identified patent and that said Letters Patent is hereby corrected as shown below:

In the Claims

Column 18 In Claim 1, Line 31, please delete "and optionally a bismuth salt" and insert -- and optionally a bismuth oxide -- therefore.

Signed and Sealed this
Fourth Day of February, 2020

Andrei Iancu
*Director of the United States Patent and Trademark Office*